US011045669B2

(12) United States Patent
Imbert et al.

(10) Patent No.: US 11,045,669 B2
(45) Date of Patent: Jun. 29, 2021

(54) **HYDROALCOHOLIC EXTRACT OF *SCHINUS MOLLE*, COSMETIC COMPOSITIONS COMPRISING THE SAME AND COSMETIC USES THEREOF**

(71) Applicants: ISP INVESTMENTS LLC, Wilmington, DE (US); JAFER, Granollers (ES)

(72) Inventors: Isabelle Imbert, Cannes (FR); Nouha Domloge, Opio (FR); Jean Marie Botto, Valbonne (FR); Rémi Laville, Drap (FR); Sébastien Garnier, Le Rouret (FR)

(73) Assignees: ISP INVESTMENTS LLC, Wilmington, DE (US); JAFER ENTERPRISES R&D, S.L., Granollers (ES)

(*) Notice: Subject to any disclaimer, the term of this patent is extended or adjusted under 35 U.S.C. 154(b) by 0 days.

(21) Appl. No.: 15/564,537

(22) PCT Filed: Apr. 5, 2016

(86) PCT No.: PCT/EP2016/057457
§ 371 (c)(1),
(2) Date: Oct. 5, 2017

(87) PCT Pub. No.: WO2016/162343
PCT Pub. Date: Oct. 13, 2016

(65) Prior Publication Data
US 2018/0078491 A1 Mar. 22, 2018

(30) Foreign Application Priority Data
Apr. 9, 2015 (FR) ...................................... 1553082

(51) Int. Cl.
*A61K 36/00* (2006.01)
*A61Q 17/00* (2006.01)
*A61Q 19/08* (2006.01)
*A61K 8/9789* (2017.01)
*A61K 8/9783* (2017.01)

(52) U.S. Cl.
CPC ............ *A61Q 17/00* (2013.01); *A61K 8/9783* (2017.08); *A61K 8/9789* (2017.08); *A61Q 19/08* (2013.01)

(58) Field of Classification Search
None
See application file for complete search history.

(56) References Cited

U.S. PATENT DOCUMENTS

2006/0018867 A1* 1/2006 Kawasaki ............ A61K 8/898
424/70.122
2013/0302419 A1 11/2013 Da Silva et al.

FOREIGN PATENT DOCUMENTS

| AR | 079996 A1 | 3/2012 |
| JP | 2000247862 A | 9/2000 |
| JP | 2000247862 A | 9/2000 |

OTHER PUBLICATIONS

Ono et al. (2008) Food Sci. Technol. Res. 14(5): 499-508. (Year: 2008).*
Website document entitled "Schinus" (available at https://en.wikipedia.org/wiki/Shinus). Downloaded Jul. 9, 2019. (Year: 2019).*
Raskin et al. (2004) Current Pharmaceutical Design, 10, 3419-3429. (Year: 2004).*
Revilla et al. (1998) J. Agric. Food Chem. 46: 4592-4597. (Year: 1998).*
Bello, R. et al., "In Vitro Pharmacological Evaluation of the Dichloromethanol Extract from *Schinus molle* L.", Phytotherapy Research, 12, pp. 523-525, 1998.
Bras, C. et al., "Evaluation of the acute dermal exposure of the ethanolic and hexanic extracts from leaves of *Schinus molle* var. *areira* L. in rats," Journal of Ethnopharmacology, 137, pp. 1450-1456, 2011.
Dominguez, X.A. et al., "Angiospermae," Phytochemistry, vol. 10, published by Pergamon Press, p. 1687, 1971.
Ferrero, A. et al., "Acute and subacute toxicity evaluation of ethanolic extract from fruits of *Schinus molle* in rats," Journal of Ethnopharmacology, 113, pp. 441-447, 2007.
Huerta, A. et al., "Toxicity and repellence of aqueous and ethanolic extracts from *Schinus molle* on elm leaf beetle *Xanthogaleruca luteola*," Crop Protection, 29, pp. 118-1123, 2010.
Lefebvre, M-A. et al., "Evaluation of the Impact of Urban Pollution on the Quality of Skin. A Multicenter Study in Mexico.", 25 pages, 2015.
Machado, D.G. et al., "Antidepressant-like effect of rutin isolated from the ethanolic extract from *Schinus molle* L. in mice: Evidence for the involvement of the serotonergic and noradrenergic systems," European Journal of Pharmacology, 587, pp. 163-168, 2008.
Malca-Garcia, G.R. et al., "Constituents from the bark resin of *Schinus molle*", Revista Brasileira de Farmacognosia, 27, pp. 67-69, 2017.
Marzouk, M.S. et al., "Antioxidant Flavonol Glycosides from *Schinus molle*," Phytotherapy Research, 20, pp. 200-205, 2006.
Pan, T-L. et al., "The impact of urban particulate pollution on skin barrier function and the subsequent drug absorption," Journal of Dermatological Science, 10 pages, 2015.

(Continued)

*Primary Examiner* — Russell G Fiebig
(74) *Attorney, Agent, or Firm* — Thompson Hine LLP

(57) ABSTRACT

The invention relates to a hydroalcoholic extract of the aerial parts of *Schinus molle*. The invention is characterised in that it comprises predominantly quercitrin and miquelianin among the extracted polyphenols, in a concentration, respectively, of at least 0.04% of quercitrin by weight of the total weight of the extract, and of at least 0.02% of miquelianin by weight of the total weight of the extract, the other extracted polyphenols, considered independently of one another, being present in trace form. The invention also relates to a method for preparing an extract of *Schinus molle* according to the invention and to cosmetic compositions comprising an effective amount of the extract according to the invention as protective active agent, and the cosmetic use of such compositions to improve the barrier function of the skin and to protect the skin against atmospheric pollutants.

5 Claims, 4 Drawing Sheets

(56) References Cited

OTHER PUBLICATIONS

Pozzo-Balbi, T. et al., "The Triterpenoid Acids of *Schinus molle*," Phytochemistry, vol. 17, pp. 2107-2110, 1978.

PubMed Clipboard, NCBI, featuring *Schinus molle*, 13 pages, Jan. 28, 2015 URL: http://www.ncbi.nlm.nih.gov/pubmed.

Terhune, S.J. et al., "β-Spathulene: A New Sesquiterpene in *Schinus molle* Oil," Phytochemistry, 13, pp. 865-866, 1974.

Yueqin, Z. et al., "Isolation of Two Triterpenoids and a Biflavanone with Anti-Inflammatory Activity from *Schnius molle* Fruits," Planta Med, 69, pp. 893-898, 2003.

PCT, International Search Report (with English translation), International Application No. PCT/EP2016/057457, 9 pages, dated May 17, 2016.

Marzouk, M.S. et al., Antioxidant Flavonol Glycosides from *Schinus molle*, Phytotherapy Research, vol. 20, pp. 200-205, XP002749056, 2006.

International Cosmetic Ingredient Dictionary and Handbook, Fifteenth Edition, vol. 2, p. 3188, XP002749057, 2 pages, 2014.

Anonymous, "Pink Pepper Extract 136825 is composed of the following Ingredients . . . ", retrieved from the internet: http://webdictionary.personalcarecouncil.org/jsp/MixtureDetailPage.jsp?ID=384167&type=M, XP002749058, 1 page, retrieved Oct. 26, 2015.

Anonymous, "*Schinus molle* extract is composed of the following ingredients . . . ", retrieved from the internet: http://webdictionary.personalcarecouncil.org/jsp/MixtureDetail.jsp?ID=399294&type=M, XP002749059, 1 page, retrieved Oct. 26, 2015.

Anonymous, "Elixiance™ biofunctional Natural and sustainable Peruvian *Schinus molle* extract with anti-pollution, skin-purifying and age-perfecting benefits," by Ashland, retrieved from the internet: https://www.ulprospector.com/documents/1392972.pdf?bs=4989&b=585194&st=20, XP002749060, 3 pages, retrieved Oct. 26, 2015.

Anonymous, "Vincience™ Biofunctionals Skin care and hair care applications," by Ashland, retrieved from the internet: https://www.ulprospector.com/documents/1183059.pdf?bs=4989&b=585194&st=20, XP002749061, 11 pages, retrieved Oct. 26, 2015.

Anonymous, "Innovation Zone 2015" in-cosmetics conference, Barcelona, Spain, XP002749062, Apr. 14-16, 2015.

\* cited by examiner

HYDROALCOHOLIC EXTRACT OF *SCHINUS MOLLE*, COSMETIC COMPOSITIONS COMPRISING THE SAME AND COSMETIC USES THEREOF

CROSS-REFERENCE TO RELATED APPLICATIONS

This application is a National Stage filing of International Application No. PCT/EP2016/057457, filed Apr. 5, 2016, which claims priority of French Patent Application No. 1553082, filed Apr. 9, 2015, which are incorporated herein by reference in their entireties.

The invention relates to a hydroalcoholic extract of *Schinus molle*, method for preparing the same, cosmetic compositions comprising the same, and cosmetic uses thereof.

*Schinus molle*, also commonly referred to as "false pepper" or "wild pepper" or "Californian pepper tree" or "Peruvian pepper", is a tree from the Anacardiacaea family, which is native to the arid zone of Northern South America and Peru's Andean deserts and can be found as far as Argentina and Chile. It has also been introduced into the majority of the world's tropical and subtropical regions.

*Schinus molle* is a quick-growing evergreen tree that grows 15 metres tall and 5 to 10 metres wide. The upper branches of the tree in particular tend to droop. The tree's leaves are arranged alternately on the stems. They generally measure 8-25 cm long and 4-9 cm wide, are finely dissected, imparipinnate, composed of numerous leaflets with uninterrupted contour and pinnate ventation, and give off a strong smell of pepper when scrunched. The tree blossoms in springtime with hanging clusters of small white flowers, located at the ends of the branches, and produces pink berries measuring 5-7 mm in diameter with a peppery smell. Its twisted and gnarled trunk has a coarse greyish bark which also gives off a peppery smell.

In traditional medicine, *Schinus molle* has been used in particular for its antibacterial and antiseptic properties in the treatment of wounds and infections (Ferreroa et al., "Acute and subacute toxicity evaluation of ethanolic extract from fruits of *Schinus molle* in rats", 2007). It appears to have also been used as an anti-depressant (Machado et al., "Antidepressant-like effect of rutin isolated from the ethanolic extract from *Schinus molle* L. in mice: Evidence for the involvement of the serotonergic and noradrenergic systems", 2008), diuretic, to ease toothache, rheumatism, and for menstrual problems. The fruits, the leaves and the sap of *Schinus molle* have also been used for their anti-hypertensive, diuretic, antispasmodic and analgesic properties (Ambasata et al., "The useful plants of India", 1986; Bello et al., "In vitro pharmacological evaluation of the dichloromethanol extract from *Schinus molle* L.", 1998).

The insecticide properties of *Schinus molle* make it suitable for consideration as an alternative to synthetic chemical products in the fight against parasites (Ferreroa et al., "Acute and subacute toxicity evaluation of ethanolic extract from fruits of *Schinus molle* in rats", 2007). To this end, the insecticide activity of aqueous and ethanolic extracts of leaves of *Schinus molle* has been tested on the elm leaf beetle (Huerta et al., "Toxicity and repellence of aqueous and ethanolic extracts from *Schinus molle* on elm leaf beetle *Xanthogaleruca luteola*", 2010). It should be noted that the aqueous extract and ethanolic extract have quite different effects, with a repellent effect for the aqueous extract, whereas the ethanolic extract has an insecticide effect.

Other publications detail the antioxidant, antimicrobial, and toxicological properties of the essential oil of *Schinus molle* (for example Martins Mdo et al., "antimicrobial and toxicological properties of *Schinus molle* L. essential oils", 2013).

Ethanolic and hexanic extracts of leaves of *Schinus molle* have been tested more particularly for their toxicity on rats in order to assess their skin toxicity (Bras et al., "Evaluation of the acute dermal exposure of the ethanolic and hexanic extracts from leaves of *Schinus molle* var. *areira* in rats", 2011). Mild, reversible skin irritation was observed here.

Patent document US2013302419 discloses that a pure methanolic or ethanolic extract of plants from the Anacardiaceae family, including *Schinus molle*, makes it possible to prepare a pharmaceutical composition used in the treatment of diseases affecting the digestive tract. The parts of the plant that can be used are the leaves, the flowers, the fruits, and preferably the bark. The extracts obtained primarily contain gallic acid.

Patent document AR 079996 describes the preparation of plant dyes from various plants including *Schinus molle* fruits. The extraction can be performed with the aid of a solvent that is miscible with water, such as methanol, ethanol or isopropanol.

The dictionary of cosmetic ingredients (International Cosmetic Ingredient Dictionary and Handbook 2014) mentions a total extract, a leaf extract, a fruit extract, and a seed extract of *Schinus molle*, however this reference does not specify the extraction conditions or the specific cosmetic effects of the cited ingredients.

The main compounds which have been isolated from *Schinus molle* are triterpenoid keto acids (Pozzo-Balbi et al., "The triterpenoid acids of *Schinus molle*", 1978). A certain number of monoterpenes, diterpenes, sesquiterpenes and triterpenes, flavonoids, gallotannins and fatty acids have been reported in *Schinus molle* (Hansel et al., "Hagers Handbuch der pharmazeutischen praxis", 1994; Terhune et al, "β-spathulene: a new sesquiterpene in *Schinus molle* oil", 1974; Dominguez et al., "Lignoceric acid and other compounds of *Schinus molle*", 1971). Another study has led to the isolation of 3 anti-inflammatory agents, 2 triterpenoid acids, and a biflavanone (Yueqin et al., "Isolation of two triterpenoids and a biflavanone with an anti-inflammatory activity from *Schinus molle* fruits", 2003).

2D-PC screening of an extract obtained by extraction in a mixture of water and 80% methanol of *Schinus molle* leaves revealed a complex mixture of glycosyl flavanols and quercitrin (Hiermann et al., "Die Untersuchung potentieller Wirkstoffe in epilobium Arten.", 1983). The publication Marzouk et al. ("Antioxidant flavonol glycosides from *Schinus molle*", 2006) has more particularly revealed, from an 80% methanol aqueous extract of *Schinus molle* leaves obtained by chromatographic separation, 2 new acylated quercitrin glycosides: isoquercitrin 6"-O-p-hydroxybenzoate and 2"-O-alpha-L-rhamnopyranosyl-hyperin 6"-O-gallate, as well as 12 polyphenol metabolites known in this species, that is to say gallic acid, methyl gallate, chlorogenic acid, 2"-alpha-L-rhamnopyranosyl-hyperin, quercitrin 3-O-beta-D-neohesperidoside, miquelianin, quercitrin 3-O-beta-D-galacturonopyranoside, isoquercitrin, hyperin, isoquercitrin 6"-gallate, hyperin 6"-O-gallate and (+)-catechin.

Numerous publications thus relate to different *Schinus molle* extracts, however none seems to disclose or even suggest a cosmetic use, more particularly for improving the barrier function of the skin and for protecting against atmospheric pollutants, for example for fighting against the appearance of signs of skin ageing.

In addition, patent document JP04176912 is known and describes a composition comprising one or more extracts of plants selected from Aguaje (*Mauritia flexuosa* L. f., Achira), (*Canna edulis* Ker Gawl.), Alg arrobo (*Prosopis pallida* DC.), Huito (*Genipa americana* L.), Oca (*Oxalis tuberosa* Mol.), Olluco (*Ullucus tuberousus* Caldas), Cupuazu (*Theobroma grandiflorum* K. Schu m.), Tarwi (*Lupinus mutabilis* Sweet), Maca (*Lepidium meyenii* Walpers), Mashua (*Trop aeolum tuberosum* Ruizet Pav.), molle (*Schinus molle* L.) and Yacon (*polymnia sonchi folia* Poepp. et Endl.). Such compositions affect water retention, for example so as to prevent skin dryness, minimise itching, and provide glowing skin and shiny hair.

However, the solvents used for soaking at ambient temperature for 3-7 days are those used conventionally by a person skilled in the art, more particularly selected from water, ethanol, 1,3-butylene glycol, propylene glycol, glycerol, and polyethylene glycol.

Patent document JP2000247862 is also known and describes the preparation of a whole plant extract from Pirul (*Schinus molle*) by soaking for 5 days in a 50/50 water-ethanol mixture. The extracts obtained have antioxidant properties and can be used as pharmaceutical or cosmetic products, for example for whitening the skin.

Considering the above, one problem which the invention aims to solve is that of developing products based on an extract of *Schinus molle* which can be used as a cosmetic, are easily produced, and, by optimisation of the physico-chemical properties, have beneficial properties for the skin whilst limiting the undesirable effects (toxicity) observed in the prior art.

In particular, the applicants have developed a method for *Schinus molle* extraction which has been optimised so as to select and ensure a high content of target molecules of interest in the obtained extract, specifically 2 polyphenols of interest, neither of which has been described before in *Schinus molle*. This development has been achieved in accordance with eco-extraction criteria (biosourced solvents, optimisation of heating temperature and stirring time, ratio of plant matter quantity/solvent quantity and type) so as to obtain the best polyphenol content/energy cost compromise (the solvent being retained advantageously in the liquid extract), and so as to increase the level of concentration of the compounds of interest in relation to the other polyphenol extracts compared to the extracts known from the prior art.

Among the types of extraction mentioned in the prior art, i.e. aqueous, methanolic, ethanolic and hexanic extraction, or extraction by steam distillation (essential oil) or supercritical $CO_2$ extraction of *Schinus molle*, none allows the selective extraction of the phenolic compounds of interest in accordance with the invention.

In fact, supercritical $CO_2$ extraction allows the extraction of the oily phase, but not of the polyphenols of interest. Likewise, an aqueous extraction extracts, for the most part, polar compounds such as polar sugars, proteins and metabolites of low molecular weight, whereas the polyphenols of interest are present only in trace form, due to their polarity. Lastly, alcoholic solvents such as methanol and ethanol non-selectively extract the polar and apolar molecules present in *Schinus molle*, such as glycoside flavanols (isoquercitrin-6"-O-p-hydroxybenzoate, 2"-O-α-L-rhamnopyranosyl-hyperin-6"-O-gallate, gallic acid, methyl gallate, chlorogenic acid, 2"-α-L-rhamnopyranosyl-hyperin, quercitrin-3-O-β-D-neohesperidoside, miquelianin, quercitrin-3-0-β-D-galacturonopyranosid, isoquercitrin, hyperin, isoquercitrin 6"-gallate, hyperin 6"-O-gallate, (+)-catechin, essential oil, steroidal triterpene, preisocalamenediol, fatty acids (linoleic, linolenic, behenic, lignoceric acids), unsaponifiables (α-amyrin, β-sitosterol), and sugars (laccase: arabinose, xylose, mannose, galactose, glucose, glucosamine).

The invention therefore firstly relates to a hydroalcoholic extract of the aerial parts of *Schinus molle*, characterised in that it comprises predominantly quercitrin and miquelianin among the extracted polyphenols in a concentration, respectively, of at least 0.04% of quercitrin by weight of the total weight of the extract and of at least 0.02% of miquelianin by weight of the total weight of the extract, the other extracted polyphenols, considered independently of one another, being present in trace form, that is to say in a concentration for each extracted polyphenol, considered individually, of less than 0.01% (100 ppm) by weight of the total weight of the extract.

In addition, the invention secondly relates to a method for obtaining an extract of *Schinus molle* according to the invention, comprising the following steps, in which:

a) the un-stripped leaves of the small stems carrying the leaves of *Schinus molle* are collected;

b) the collected, fresh or dried, un-stripped leaves of the small stems carrying the leaves of *Schinus molle* are dispersed, in a proportion of from 0.1% to 20% by weight of solid matter relative to the total weight used, in a hydroalcoholic solvent, the alcohol being selected from ethanol, glycerol, or propanediol, in a proportion between 10% and 90% by weight of alcohol relative to the total weight of the solvent;

c) a solid-liquid extraction is performed, with stirring, at a temperature between 4 and 100° C. for a period between 10 minutes and 4 hours;

d) the liquid and solid phases are separated so as to remove the solid phase and recover a liquid hydroalcoholic extract of *Schinus molle* comprising primarily quercitrin and miquelianin from the extracted polyphenols in a concentration, respectively, of at least 0.04% of quercitrin by weight of the total weight of the extract, and of at least 0.02% of miquelianin by weight of the total weight of the extract, the other extracted polyphenols, considered independently of one another, being present in trace form, that is to say in a concentration for each extracted polyphenol, considered individually, of less than 0.01% (100 ppm) by weight of the total weight of the extract; and e) optionally, when the alcohol is ethanol, the obtained liquid extract of *Schinus molle* is dried so as to obtain a solid extract of *Schinus molle*.

The invention thirdly relates to a cosmetic composition, characterised in that it comprises, as protective active agent, an effective amount of an extract of *Schinus molle* according to the invention and a physiologically acceptable excipient.

Lastly, the invention fourthly relates to the cosmetic use of a composition according to the invention for improving the barrier function of the skin and for protecting the skin against atmospheric pollutants.

The invention and the advantages resulting therefrom will be better understood upon reading the following description and non-limiting embodiments, prepared with regard to the accompanying drawings, in which.

Figure 1:
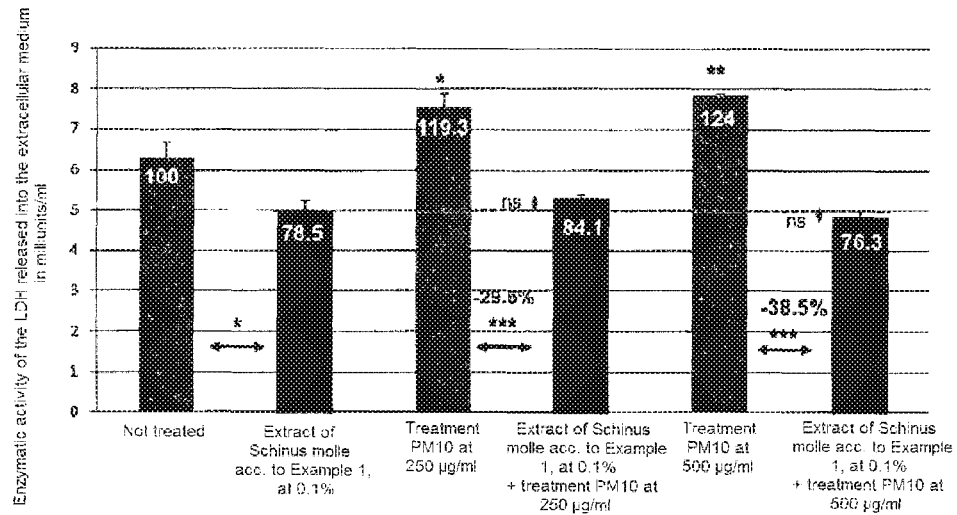
FIG. 1 shows the evaluation of the protective effect of an extract of *Schinus molle* according to the invention on keratinocytes exposed to an environmental stress by PM10-like polluting particles.

In this description, unless specified otherwise, it is understood that when a range is given, this includes the upper and lower limits of said range.

The invention relates to a hydroalcoholic extract of the aerial parts of *Schinus molle* comprising predominantly quercitrin and miquelianin among the extracted polyphenols in a concentration, respectively, of at least 0.04% of quercitrin by weight of the total weight of the extract, and of at least 0.02% of miquelianin by weight of the total weight of the extract, the other extracted polyphenols, considered independently of one another, being present in trace form.

Among the 2 polyphenols predominantly extracted in accordance with the invention, quercitrin, which is a known flavanol glycoside, has never before been cited in the composition of *Schinus molle*, more particularly the aerial parts thereof.

The other extracted polyphenols include those commonly present in *Schinus molle*, such as isoquercitrin for example.

The term 'trace form' means a concentration for each extracted polyphenol, considered individually, of less than 0.01% (100 ppm) by weight of the total weight of the extract. The aerial parts of *Schinus molle* denote the leaves as such and also the un-stripped leaves of the small stems carrying the leaves. In the description, the terms "aerial parts" and "un-stripped leaves of the small stems carrying the leaves" will be used synonymously.

The extracts of *Schinus molle* according to the invention, however, are very difficult to characterise as such because their composition varies, for the same species, in accordance with different factors, such as the parts of *Schinus molle* used, the place of harvest, the method of harvest, the climatic conditions, and the year of harvest.

Advantageously, the *Schinus molle* preferably used in accordance with the invention is cultivated in zones far from urban pollutions, for example at altitude in South America, the extract obtained in accordance with the invention comprising no micro-polluting elements such as phthalates, pesticides, polycyclic aromatic hydrocarbons, or heavy metals. It is more particularly harvested from June to September.

The extract according to the invention is obtained from fresh or dried un-stripped leaves of the small stems carrying the leaves of *Schinus molle* by solid-liquid extraction, with stirring, of from 0.1% to 20% by weight of solid matter relative to the total weight used, in a hydroalcoholic solvent, the alcohol being selected from ethanol, glycerol, or propanediol, in a proportion between 10% and 90% by weight of alcohol relative to the total weight of the solvent, at a temperature between 4 and 100° C., for a period between 10 minutes and 4 hours, under vacuum, at atmospheric pressure or under pressure, advantageously at atmospheric pressure, and by separation of the liquid and solid phases so as to remove the solid phase and recover a liquid extract of *Schinus molle*.

The term "fresh" means the phase after collection during which the plant has a humidity similar to that of the plant before picking.

The term "drying" means the phase after collection, during which the plant is dehydrated to a humidity said to be a safeguard humidity. The objective of this drying process is to sufficiently reduce the content of water in particular of the un-stripped leaves of the small stems carrying the leaves in order to ensure favourable conditions of storage or subsequent transformation of the plant.

By way of example, the un-stripped leaves of the small stems carrying the leaves can be dried naturally by exposure to air (in sunlight or in the shade) by controlling the relative humidity for a period of at most 10 to 20 days or advantageously can be delicately dried artificially using air blown by a dryer, hot air generator, or fan, at a temperature between 20° C. and 40° C.

Preferably, after having been advantageously washed, the un-stripped leaves of the small stems carrying the leaves are dried, and used whole or ground, preferably ground or cryogenically ground.

After the step of collection, optionally washing, and advantageously drying then grinding of the un-stripped leaves of the small stems carrying the leaves of *Schinus molle*, a step of dispersion and extraction in a hydroalcoholic solvent is performed.

The extraction is performed advantageously always with stirring, thus allowing a dispersion and a homogenisation of the solid and liquid, effectively improving the diffusion of the solute in the solvent.

The water used for the extraction is a distilled water, demineralised water, or a water rich in mineral salts and/or oligo elements, preferably a distilled water.

In order to extract predominantly the quercitrin and miquelianin of interest among the extracted polyphenols of *Schinus molle*, an alcoholic co-solvent selected from ethanol, glycerol or propanediol, for example 1,2-propanediol or 1,3-propanediol, preferably 1,3-propanediol, in a proportion between 10% and 90% by weight of alcohol relative to the total weight of the solvent is used.

The hydroalcoholic solvent is preferably a water-alcohol mixture in a proportion between 50% and 80% by weight of alcohol relative to the total weight of the solvent, even more preferably between 60% and 80% when the alcohol is ethanol or propanediol.

The solid-liquid extraction is preferably performed at a temperature between 10 and 80° C., more preferably between 20 and 70° C., for a period between 30 minutes and 3 hours, more preferably between 1 hour and 2 hours.

The extract according to the invention is preferably obtained from 1% to 15%, more preferably from 5% to 10%, by weight of solid matter relative to the total weight used.

At the end of the extraction, the remaining plant matter depleted of compounds of interest is advantageously separated from the liquid phase, for example by decanting, by centrifugation, or by clarifying filtration.

The liquid phase obtained can be microfiltered with the aid of filtering media of appropriate porosity in order to obtain a clear solution devoid of solid plant particles.

This step of liquid-solid separation can be followed advantageously by one or more steps of purification, for example by microfiltration, ultrafiltration and/or nanofiltration, making it possible to concentrate the compounds of interest at the expense of other extracted compounds, such as proteins and polysaccharides, as well as the solvent.

The duration and method of extraction thus play a key role for the extracted substances, that is to say predominantly quercitrin and miquelianin among the extracted polyphenols, the other extracted polyphenols being present in trace form.

The hydroalcoholic extraction for a necessary and sufficient time makes it possible to advantageously solubilise the quercitrin and the miquelianin in the extract in an effective amount for their anti-ageing protective properties.

Although the alcoholic co-solvents used in accordance with the invention have the same solvent capability, the alcoholic co-solvent preferably used is glycerol or propanediol, more preferably propanediol, even more preferably 1,3-propanediol.

In accordance with a first advantageous embodiment of the invention, such alcoholic co-solvents (glycerol or propanediol) make it possible to obtain a liquid extract in which the co-solvent is retained. The extract obtained is thus physiologically acceptable and can be used directly for cosmetic applications.

In accordance with a second embodiment of the invention, when the alcohol is ethanol the obtained liquid extract of *Schinus molle* is preferably dried for example by atomisation, lyophilisation, or zeodration (dehydration using zeolites) so as to obtain a solid extract of *Schinus molle*, the ethanol being evaporated.

The drying can be performed in the presence of a support, such as maltodextrin.

To this end, in accordance with another aspect, the invention relates to a method for obtaining an extract of *Schinus molle* according to the invention comprising the steps as described further above, advantageously in accordance with the first or the second embodiment.

The method for obtaining an extract of *Schinus molle* according to the invention preferably comprises the following steps, in which:

a) the un-stripped leaves of the small stems carrying the leaves of *Schinus molle* are collected;

b) the collected, fresh or dried, un-stripped leaves of the small stems carrying the leaves of *Schinus molle* are dispersed, in a proportion of from 0.1% to 20% by weight of solid matter relative to the total weight used, in a hydroalcoholic solvent, the alcohol being selected from ethanol, glycerol, or propanediol, in a proportion between 10% and 90% by weight of alcohol relative to the total weight of the solvent;

c) a solid-liquid extraction is performed, with stirring, at a temperature between 4 and 100° C. for a period between 10 minutes and 4 hours, under vacuum, at atmospheric pressure or under pressure, preferably at atmospheric pressure;

d) the liquid and solid phases are separated, for example by decanting, centrifugation, or clarifying filtrations, so as to remove the solid phase and recover a liquid hydroalcoholic extract of *Schinus molle* comprising primarily quercitrin and miquelianin from the extracted polyphenols in a concentration, respectively, of at least 0.04% of quercitrin by weight of the total weight of the extract, and of at least 0.02% of miquelianin by weight of the total weight of the extract, the other extracted polyphenols, considered independently of one another, being present in trace form, that is to say in a concentration for each extracted polyphenol, considered individually, of less than 0.01% (100 ppm) by weight of the total weight of the extract; and e) optionally, when the alcohol is ethanol, the obtained liquid extract of *Schinus molle* is dried so as to obtain a solid extract of *Schinus molle*.

The liquid extract of *Schinus molle* thus obtained can be purified by microfiltration, ultrafiltration and/or nanofiltration to concentrate the extract of quercitrin and miquelianin relative to the proteins and polysaccharides also extracted.

By way of illustration, preferred practical examples the invention will be described below.

EXAMPLE 1: PREPARATION OF A HYDROGLYCOLIC EXTRACT FROM THE AERIAL PARTS OF *SCHINUS MOLLE*

The un-stripped leaves of the small stems carrying the leaves of *Schinus molle*, dried beforehand, are cryogenically ground in a knife mill comprising a 1 mm grate, which makes it possible to obtain a powder of which the size of the particular is predominately towards 500 µm.

The powder (150 g) thus obtained is then placed in a glass reactor, equipped with a stirrer and double jacketed heating with the aid of a heat transfer fluid.

The solvent used (1350 g) for the soaking is a mixture of 70% of 1,3-propanediol (DuPont Tate & Lyle Bio Products Company) and 30% of distilled water.

The powder of un-stripped leaves of the small stems carrying the leaves is dispersed in the solvent for 2 hours at 50° C., then the mixture is filtered.

The extract thus obtained in solvent medium, that is to say 945 g, is then assayed by the Folin-Ciocalteu method, which makes it possible to assay all the polyphenols. The method uses gallic acid as standard and the results are expressed in gallic acid equivalent mass %. This extract thus contains 0.43% m/m gallic acid equivalent of total polyphenols, and more particularly 0.1% m/m of quercitrin and 0.06% m/m of miquelianin for a dry extract of 2.4% m/m, that is to say 18% of total polyphenols, including 4.2% quercitrin and 2.5% miquelianin in the dry extract.

EXAMPLE 2: PREPARATION OF A HYDROETHANOLIC EXTRACT FROM THE AERIAL PARTS OF *SCHINUS MOLLE*

The un-stripped leaves of the small stems carrying the leaves of *Schinus molle*, dried beforehand, are cryogenically ground in a knife mill comprising a 1 mm grate, which makes it possible to obtain a powder of which the size of the particles is predominately towards 500 µm.

The powder (150 g) thus obtained is placed in a glass reactor, equipped with a stirrer and double jacketed heating with the aid of a heat transfer fluid.

The solvent used (1350 g) for the soaking is a mixture of 70% ethanol and 30% distilled water.

The powder of un-stripped leaves of the small stems carrying the leaves is dispersed in the solvent for 2 hours at 50° C., then the mixture is filtered.

The ethanolic extract is evaporated on a rotovap so as to remove the majority of the solvent, then lyophilised so as to obtain a solid that will then be ground.

13 g of dry extract of un-stripped leaves of the small stems carrying the leaves of *Schinus molle*, assayed by the Folin-Ciocalteu method and containing 14% (gallic acid equivalent) of total polyphenols, more particularly 4% quercitrin and 2% miquelianin in the dry extract, were thus obtained.

By comparison, the applicants performed other extraction methods making it possible to obtain an extract of *Schinus molle*.

For example, an ethanolic extract, obtained by extraction in pure ethanol of un-stripped leaves of the small stems carrying the leaves of *Schinus molle* performed in conditions comparable to those of Example 2 above, makes it possible to obtain a dry extract containing only 8% of total polyphenols, and more particularly 3% quercitrin and 1.2% miquelianin in the dry extract.

The method according to the invention, and in particular the choice of the hydroalcoholic solvent, makes it possible to considerably limit or even avoid an extraction of the fatty fraction extracted from the leaves of *Schinus molle* with the solely alcoholic solvent (100%) and thus to concentrate the extracted polyphenols.

According to these results, it can be noted that the extraction method, which is easily implemented, is essential to obtain an extract of *Schinus molle* which comprises predominantly quercitrin and miquelianin among the extracted polyphenols in a concentration, respectively, of at least 0.04% quercitrin by weight of the total weight of the extract and at least 0.02% of miquelianin, the other extracted polyphenols, considered independently of one another, being present in trace form, and which can thus be used as a cosmetic.

The predominantly extracted polyphenols contained in the extract of *Schinus molle* according to the invention are more particularly anti-ageing active agents which act in particular to improve the barrier function of the skin and to protect the skin against atmospheric pollutants.

In fact, the tissues in contact with the external medium, such as the skin, the hair, the nails and the lungs, are directly and constantly exposed to the pollutants present in the environment, these being potentially harmful.

Within the scope of the invention the term 'atmospheric pollutants' denotes the pollutants present in the environment which are harmful to health and are present in particular in the form of gases and breathable particles. They can be present outdoors, for example diesel engine particles, ozone, or heavy metals, and/or inside homes, where the pollution can be caused in particular by cigarette smoke or by solvents released by paints, glues or wallpapers, such as toluene, styrene, xylene and benzaldehyde.

Among the pollutants present in the environment, a distinction is made between primary pollutants, which are directly produced by sources of pollution (road traffic, industries, heating, agriculture, etc.), and secondary pollutants, which originate from chemical reactions between gases. Among the primary pollutants, mention can be made for example of carbon oxides, sulphur oxides, nitrogen oxides, light hydrocarbons, volatile organic compounds (VOCs), metals (lead, mercury, cadmium, etc.), and fine or ultrafine particles, such as PM10 particles (with a diameter less than 10 μm) and PM2.5 particles (with a diameter less than 2.5 μm), which can be particularly toxic due to their ability to penetrate deeply into the respiratory, cardiovascular and cutaneous systems, their size being smaller than the size of the pores of human skin. Secondary pollutants include secondary particles, ozone, and nitrogen oxides.

The extraction according to the invention makes it possible to obtain a clear extract that is enriched in active anti-ageing compounds, devoid of solid plant particles, advantageously stable in terms of appearance, colour and smell, and that can be used in the formulation of cosmetic compositions.

In accordance with a third aspect of the invention, the extract of *Schinus molle* is used in the composition of a cosmetic product comprising, as protective active agent, an effective amount of an extract of *Schinus molle* according to the invention, and a physiologically acceptable excipient.

The term 'effective amount' denotes the minimum amount of extract according to the invention which is necessary to obtain the activity, in particular barrier function and protection of the skin against atmospheric pollutants, without this amount being toxic.

The extract of *Schinus molle* is advantageously present in the composition in a concentration of from 0.001 to 1% by weight relative to the total weight of the composition, preferably from 0.01 to 1%.

Even more preferably, the composition according to the invention predominantly comprises quercitrin and miquelianin and substantially does not comprise any other polyphenols or only comprises these in trace form among the extracted polyphenols.

A physiologically acceptable excipient denotes a vehicle suitable for being contacted with the outer layers of the skin or mucous membranes, that is to say which does not present any toxicity and which does not cause any irritation, undue allergic response, or intolerance reaction.

A physiologically acceptable excipient can comprise one or more compounds.

The composition usable in accordance with the invention could be applied in any appropriate manner, in particular orally, or by external topical application, and the formulation of the compositions will be adapted accordingly by a person skilled in the art.

The compositions according to the invention are preferably present in a form suitable for topical application. These compositions must therefore contain a physiologically acceptable medium, that is to say a medium compatible with the skin and appendages, with no risk of discomfort during their application and which cover all suitable cosmetic forms.

The term 'topical application' means applying or spreading the extract of *Schinus molle* according to the invention, and more particularly a composition containing said extract, on the surface of the skin or a mucous membrane.

The term 'skin' denotes more particularly the skin of the face, in particular the contour of the eyes and the mouth, the nose, the forehead, the neck, the hands, and also the skin of the rest of the body.

The compositions for carrying out the invention can be present in particular in the form of an aqueous, hydroalcoholic, or oily solution, an oil-in-water emulsion, a water-in-oil emulsion, or multiple emulsions; the compositions can also be present in the form of suspensions, or powders, suitable for application to the skin, the mucous membranes, the lips and/or the hair.

These compositions can be more or less fluid and can also have the appearance of a cream, a lotion, a milk, a serum, an ointment, gel, a paste, or a mousse. They can also be present in solid form, such as 5898 a stick, or can be applied to the skin in the form of an aerosol.

For example, additives necessary for the formulation, such as solvents, thickeners, diluents, antioxidants, dyes, solar filters, self-tanning agents, pigments, fillers, preservatives, perfumes, odour absorbers, essential oils, vitamins, essential fatty acids, surfactants, filmogenic polymers, etc., can be mentioned by way of example as potential physiologically acceptable excipient commonly used in the envisaged field of application.

In any case, a person skilled in the art will ensure that these additives and the proportions thereof are selected so as not to be detrimental to the sought advantageous properties of the composition according to the invention. These additives, for example, can correspond to 0.01 to 20% of the total weight of the composition. When the composition according to the invention is an emulsion, the fatty phase can represent from 5 to 80% by weight and preferably from 5 to 50% by weight relative to the total weight of the composition. The emulsifiers and co-emulsifiers used in the composition are selected from those used conventionally in the field in question. For example, they can be used in a proportion ranging from 0.3 to 30% by weight relative to the total weight of the composition.

In accordance with another advantageous embodiment of the invention, the extract of *Schinus molle* according to the invention can be encapsulated or enclosed in a cosmetic vector such as liposomes or any other nanocapsule or microcapsule used in the field of cosmetics, or adsorbed on powdery organic polymers, or mineral supports, such as talcs and bentonite.

The composition according to the invention can advantageously comprise, besides the active agent according to the invention, at least one other active agent having cosmetic effects similar and/or complementary to those of the invention. In accordance with the invention, this active agent is defined as an "additional active agent".

For example, the one or more additional active agents can be selected from: anti-ageing agents, firming agents, brightening agents, hydrating agents, draining agents, agents promoting microcirculation, pharmaceutical agents, exfoliants, peeling agents, agents stimulating the extracellular matrix, agents activating the energy metabolism, antibacterial agents, antifungal agents, soothing agents, anti-free radical agents, anti-UV agents, anti-acne agents, anti-inflammatory agents, anaesthetic agents, agents giving a sensation of heat, agents giving a sensation of freshness, and slimming agents.

Such additional agents can be selected from the group comprising:
vitamin A and in particular retinoic acid, retinol, retinol propionate, retinol palmitate;
vitamin B3, more particularly niacinamide, tocopherol nicotinate;
vitamin B5, vitamin B6, vitamin B12, panthenol;
vitamin C, in particular ascorbic acid, ascorbyl glucoside, ascorbyl tetrapalmitate, magnesium and sodium ascorbyl phosphate;
vitamins E, F, H, K, PP, the coenzyme Q10;
inhibitors of metalloproteinase, or an activator of TIMPs;
DHEA, precursors and derivatives thereof;
amino acids, such as arginine, ornithine, hydroxyproline, hydroxyproline dipalmitate, palmitoylglycine, hydroxylysine, methionine, and derivatives thereof, N-acyl amino acid compounds;
natural or synthetic peptides, including di-, tri-, tetra-, penta- and hexapeptides and the lipophilic and isomeric derivatives thereof, and derivatives thereof complexed with other species, such as a metal ion (e.g. copper, zinc, manganese, magnesium, and others). By way of example, mention can be made of the peptides known commercially under the name MATRIXYL®, ARGIRELINE®, CHRONOGEN™, LAMINIXYL IS™, PEPTIDE Q10™, COLLAXYL™ (patent FR2827170, ASHLAND®), PEPTIDE VINCI 01™ (patent FR2837098, ASHLAND®), PEPTIDE VINCI 02™ (patent FR2841781, ASHLAND®), AlPeptide™ (patent FR2846883, ASHLAND®) or the synthetic peptide of sequence Arg-Gly-Ser-NH$_2$, sold under the name AlPeptide™ by ASHLAND®;
the extract of *Artémia salina*, sold under the name GP4G™ (FR2817748, ASHLAND®);
plant peptide extracts, such as the extracts of flax (Lipigenine™, patent FR2956818, ASHLAND®), the extracts of soya, spelt, vine, rape, flax, rice, corn, pea;
yeast extracts, for example Dynagen™, (patent FR2951946, ASHLAND®) or Actopontine™ (patent FR2944526, ASHLAND®);
dehydroacetic acid (DHA);
phytosterols of synthetic or natural origin;
salicylic acids and derivatives thereof, the alpha- and beta-hydroxy acids, the silanols;
the amino sugars, glucosamine, D-glucosamine, N-acetyl glucosamine, N-acetyl-D-glucosamine, mannosamine, N-acetyl mannosamine, galactosamine, N-acetyl galactosamine;
the extracts of polyphenols, isoflavones, and flavonoids, such as grape extracts, pine extracts, olive extracts;
the lipids, such as the ceramides or phospholipids, oils of animal origin, such as squalene or squalane; vegetable oils such as sweet almond oil, coconut oil, castor oil, jojoba oil, olive oil, rape oil, peanut oil, sunflower oil, wheat germ oil, corn germ oil, soya oil, cotton oil, alfalfa oil, poppy oil, pumpkin oil, primrose oil, millet oil, barley oil, rye oil, safflower oil, passionflower oil, hazelnut oil, palm oil, apricot kernel oil, avocado oil, calendula oil; ethoxylated vegetable oils, Shea butter;
all UV screens and solar filters;
cyclic AMP and derivatives thereof, agents that activate the adenylate cyclase enzyme and agents which are inhibitors of the phosphodiesterase enzyme, *Centella asiatica* extract, asiaticoside Asiatic acid, xanthine methyls, theine, caffeine and derivatives thereof, theophylline, theobromine, forskolin, esculin and esculoside, ACE inhibitors, the peptide Val-Trp, inhibitors of the neuropeptide Y, encephalin, *gingko biloba* extract, *dioscorea* extract, rutin, yerba mate extract, guarana extract, the oligosaccharides, the polysaccharides, carnitine, ivy extract, rockweed extract, Prunella vulgaris hydrolysed extract, *Celosia cristata* hydrolysed extract, *Anogeissus leiocarpus* extract, extract of leaves of *Manihot utilissima*, palmitoylcarnitine, carnosine, taurine, elderberry extract, algae extracts, such as *Palmaria* Palmat extracta.

By way of illustration, en exemplary formulation of a cosmetic composition containing an extract of *Schinus molle* obtained in accordance with the invention is mentioned hereinafter:

EXAMPLE 3: BEAUTY CREAM (FORMULA REFERENCE #TCAAE08)

| Ingredients (Brand name) | INCI | mass % |
| --- | --- | --- |
| Phase A | | |
| Purified water | Aqua | QSP 100 |
| Na4 EDTA | Tetrasodium EDTA | 0.05 |
| Lubrasil ™ II DM hydrogel | Glycerin (and) Glyceryl Acrylate/Acrylic Acid Copolymer (and) Laureth-23 (and) Dimethicone | 3.00 |
| Liquapar/Rokonsal ™ MEP preservative | Phenoxyethanol (and) Methylparaben (and) Ethylparaben (and) Propylparaben | 1.00 |
| Phase B | | |
| UltraThix ™ P-100 polymer | Acrylic Acid/VP Crosspolymer | 0.60 |
| Phase C | | |
| Sodium hydroxide | Sodium Hydroxide | 0.02 |
| Purified water | Aqua | 0.50 |
| Phase D | | |
| Belsil* W3230 | Bis-Stearoxydimethylsilane, stearyl alcohol, Dimethicone | 2.00 |
| Simulsol* 165 | PEG-100 Stearate (and) Glyceryl Stearate | 2.00 |
| Refined Shea butter | Butyrospermum Parkii (Shea) Butter | 2.00 |
| Ceraphyl ™ 28 ester | Cetyl Lactate | 1.50 |

| Ingredients (Brand name) | INCI | mass % |
|---|---|---|
| Ceraphyl ™ 791 ester | Isocetyl Stearoyl Stearate | 2.00 |
| Ceraphyl ™ ODS ester | Octyldodecyl Stearate | 3.00 |
| Ceraphyl ™ 368 ester | Ethylhexyl Palmitate | 4.00 |
| Phase E | | |
| Sodium hydroxide | Sodium Hydroxide | 0.03 |
| Purified water | Aqua | 0.50 |
| Phase F | | |
| Extract of *Schinus molls* according to Example 1 | | 1.00 |

Method for preparing the composition of Example 3:
1. Add phase A to the primary container and start to homogenise. Heat to 70-75° C.
2. Sprinkle in an UltraThix™ P-100 and mix well for approximately 30 minutes.
3. Add the ingredients of phase D to a separate beaker and heat to 70-75° C.
4. Add phase C, pre-mixed, to phase A and mix until homogeneous.
5. Hold at 70-75° C. and add phase D to the primary container and mix well. The emulsion must be homogeneous.
6. Start the cooling.
7. At approximately 50° C., add phase E, pre-mixed, and mix well.
8. At ambient temperature, add phase F and mix until uniform. Stop at 25° C.

The composition according to Example 3 is present in the form of a stable white cream with a pH between 5.20 and 5.80 and a viscosity (D0) of 25000-45000 (Brookfield RVT/Spindle B/5 RPM/1 minute/25° C.)

A composition said to be a "placebo" composition is produced exactly in the same way with the exception that the ingredient "extract of *Schinus molle* according to Example 1" is replaced by purified water. This "placebo" composition is more particularly used as a control in some of the activity tests below.

In accordance with another aspect, the invention relates to the cosmetic use of a composition comprising in particular an effective amount of an extract of *Schinus molle* obtained in accordance with the invention in order to improve the barrier function of the skin and to protect against atmospheric pollutants.

The skin is an organ of which the upper part, the stratum corneum and also the hydrolipid film that covers it, has the role of a protective physical barrier with respect to the external environment. This barrier role, more commonly referred to as the "barrier function of the skin", is of major importance in tissue homeostasis and more particularly in the protection against external agents of pathogenic or non-pathogenic nature, such as environmental atmospheric pollutants.

It is known that changes to the barrier function result from external stresses such as UV rays. The consequences are significant in terms of a loss of cellular cohesion and mechanical integrity. Some enzymes involved in the terminal phases of keratinocyte differentiation play a key role in the protection against UV rays. Modifications of the expression and/or activity of these enzymes have significant consequences on the integrity of the barrier function and homeostasis of the skin.

Changes to the barrier function are also observed in cases of pathological skins and in cases of healthy aged skins, caused by anomalies in respect of the lipid synthesis, which usually create a lack of cohesion of the cells in the superficial layers of the epidermis, which may lead to an increase in skin permeability. Thus, for example, the lack of cohesion of the cells of the epidermis manifesting itself during the course of skin ageing can result in angular micro-fractures and an enlargement of the pores of the skin.

Changes to the barrier function can be caused by chemical stresses. In this last category, it is necessary to take into consideration the environmental atmospheric pollutants and more particularly the PM2.5 microparticles produced by diesel engines, the burning of coal, and the smoking of cigarettes. These microparticles, of small size, are in fact responsible for the majority of the negative effects attributed to pollution due to their ability to deeply penetrate (Pan T-L et al. The impact of urban particulate pollution on skin barrier function and the subsequent drug absorption. J Dermatol Sci, 2015).

In addition, some of these environmental atmospheric pollutants have properties that are irritating for the skin or that can cause inflammatory reactions. Inflammation could be responsible for an increased secretion of sebum (Lefebvre M. A. et al. "Evaluation of the impact of urban pollution on the quality of skin: a multicentre study in Mexico, Int J Cosmet Sci. 2015 Feb. 6).

The skin is thus regularly exposed on a daily basis to environmental stresses (UV, pollution, etc.), which can alter the physiological functioning of this barrier organ (Pan T-L et al. The impact of urban particulate pollution on skin barrier function and the subsequent drug absorption. J Dermatol Sci, 2015).

The composition according to the invention comprising an effective amount of an extract of *Schinus molle* makes it possible to fight against these external stresses by promoting a differentiation and optimal cohesion of the skin layers, making it possible to maintain a functional histological structure and a physiological permeability necessary for maintaining this essential barrier provided by the skin function at tissue level and beyond, for the organism as a whole.

The composition according to the invention is thus involved in the hydration of the skin and in the fight against the appearance of the signs of skin ageing.

The expression "signs of skin ageing" means any changes to the external appearance of the skin caused by ageing, for example wrinkles and fine lines, crevices, bags beneath the eyes, dark rings, withering, loss of skin elasticity and/or tone, loss of colour or loss of glow, pigment-related defects, but also any internal changes of the skin which are not translated systematically into a modified external appearance, for example a thinning of the skin, or any internal damage to the skin following exposure to UV rays.

The composition according to the invention is thus also used to limit sebum secretion and to reduce the size of the pores of the skin.

To this end, the invention is illustrated hereinafter by the different results of tests performed.

EXAMPLE 4: EFFECTS OF A HYDROETHANOLIC EXTRACT OF *SCHINUS MOLLE* OBTAINED IN ACCORDANCE WITH EXAMPLE 2 ON THE EXPRESSION OF MARKERS OF DIFFERENTIATION, HYDRATION, AND LIPID SYNTHESIS IN KERATINOCYTES (IN VITRO MODELS)

The potential effects of a hydroethanolic extract of *Schinus molle* obtained in accordance with Example 2 on skin hydration and barrier function were studied in a model of normal human epidermal keratinocytes (NHEKs) by analysing the expression profile of genes specific to the differentiation of keratinocytes and lipid synthesis by an RT-qPCR (reverse transcription quantitative polymerase chain reaction) method.

Biological Models:
Normal Human Epidermal Keratinocytes (NHEKs)
Cell type: $3^{rd}$ passage NHEKs Culture conditions: 37° C., 5% $CO_2$
Culture medium: keratinocyte SFM (serum free medium) supplemented with
  epidermal growth factor (EGF) 0.25 ng/ml
  pituitary extract (PE) 25 µg/ml
  gentamicin 25 µg/ml
Test medium: keratinocyte SFM supplemented with gentamicin 25 µg/ml
Tested Compounds
  Hydroethanolic extract of *Schinus molle* obtained in accordance with Example 2, in powdered form, stored at ambient temperature;
  10% stock solution (100 mg/ml) in DMSO (dimethyl sulfoxide); Concentrations tested: 0.0001%; 0.0003% and 0.001% on NHEK.
Culture and Treatment
  The normal human epidermal keratinocytes (NHEKs) were seeded and cultivated in culture medium for 24 hours. The medium was then replaced by the test medium containing, or not (control), the hydroethanolic extract of *Schinus molle* obtained in accordance with tested Example 2 or the positive reference of differentiation (1.5 mM calcium chloride), and the cells were incubated for 24 hours. All the conditions were performed with n=3.
  At the end of the incubation, the culture supernatants were removed and the cell layers were rinsed with a PBS (phosphate buffered saline) solution. The plates were immediately frozen dry at −80° C.
Analysis of the Differential Expression of the Markers by PCR Array:
  The expression of the markers was assessed by RT-qPCR on the mRNAs (messenger RNAs) extracted from the cell layers of each treatment (the replicates were pooled before the RNA extraction).
  The analysis of the expression of the genes was performed with n=2 with the aid of 2 "marker quantitative PCR arrays" containing 16 genes, including 2 housekeeping (HK) genes, dedicated to research and adapted to the screening format (mQPA-NHEK-BARRIER-16, product by BIOalternatives®).
Reverse Transcription
  The total RNAs of each sample were extracted with the aid of TriPure Isolation Reagent® in accordance with the protocol specified by the manufacturer. The amount and quality of the RNAs were evaluated by capillary electrophoresis (Bioanalyzer 2100, Agilent).
  The potentially contaminating DNA traces were removed by treatment with the DNA-free system (Ambion). The cDNAs (complementary deoxyribonucleic acids) were synthesised by reverse transcription of the total RNAs (ribonucleic acids) in the presence of oligo(dT) and the "Transcriptor Reverse Transcriptase" (Roche®) enzyme. The cDNA obtained was quantified by spectrophotometry (Nanovue; GE Healthcare®), then the cDNA amounts were adjusted.
Quantitative PCR
  The PCR reactions (polymerase chain reactions) were performed by quantitative PCR (Light Cycler; Roche Molecular Systems Inc.) and in accordance with the procedures recommended by the manufacturer.
  The reaction mixture (10 µl final) for each sample contained: 2.5 µl of cDNA,
  the primers of the different markers used,
  the reaction mixture containing the taq DNA polymerase enzyme, and
  the marker SYBR Green I, and $MgCl_2$.
  The raw quantitative PCR data were transferred and processed using the software Microsoft Excel®.
  The incorporation of fluorescence in the amplified DNA is measured continuously during the course of the PCR cycles. These measurements make it possible to obtain intensity curves of the fluorescence depending on the PCR cycles and to thus evaluate a value of relative expression (RE) for each marker. The number of cycles is determined on the basis of "exit" points of the fluorescence curves. For the same analysed marker, the later a sample exits (appeared late, after a number of increased cycles), the lower is the initial number of copies of the mRNA.
  The RE (relative expression) value is expressed in arbitrary units (AU) in accordance with the following formula:

$$(\tfrac{1}{2}^{number\ of\ cycles}) \times 10^6$$

The "mQPA-NHEK-BARRIER-16" PCR arrays contain 2 reference genes ("housekeeping" genes) used for the normalisation of the data. These 2 housekeeping genes, that is to say the RPS28 (ribosomal protein S28) and GAPDH (glyceraldehyde-3-phosphate dehydrogenase) genes, are expressed constitutively and their level of expression is not affected or is only slightly affected by the treatments. Thus, the level of expression of each marker is compared to the average expression of these 2 reference genes.
Data Processing
  The raw data were transferred and processed using the software Microsoft Excel®.
Formulas Used in this Context:

Standard mean error: sme=standard deviation $(Sd)/\sqrt{n}$

The standard mean error (sme) represents the mean deviation of the sample in relation to the mean of the true population. The sme is calculated by dividing the standard deviation (Sd) by the square root of the size of the sample.
Results
  The results are presented in Tables 1 and 2 below.
  "$CaCl_2$": complete results (number of cycles and percentage of the control) and effects of the reference ($CaCl_2$) on the expression of the different markers studied sorted by the "cluster" method;
  "hydroethanolic extract of *Schinus molle* obtained in accordance with Example 2": complete results (number of cycles and percentage of the control) and effects of this compound on the expression of the genes, sorted by the "cluster" method.
Tables 1 and 2: Effects of a Hydroethanolic Extract of *Schinus molle* According to Example 2 on the Expression of Differentiation Markers, Hydration, and Lipid Synthesis in Keratinocytes Evaluated by an RT-qPCR Method

TABLE 1

| | | | | | 0.0001% | | 0.0003% | | 0.001% | |
|---|---|---|---|---|---|---|---|---|---|---|
| mQPA-NHEK-BARRIER-16 | Genes Full name and abbreviation | | Control Cycles | Cycles | % Control (mean HK)) 100 | Cycles | % Control (mean HK) 100 | Cycles | % control (mean HK) 100 |
| Housekeeping genes (HK) | Ribosomal protein S28 | RPS28 | 18.79 18.81 | 19.29 19.29 | 86 | 19.34 19.22 | 89 | 19.52 19.50 | 80 |
| | Glyceraldehyde- | GAPDH | 16.77 | 17.02 | 103 | 17.10 | 103 | 17.22 | 105 |

TABLE 1-continued

Hydroethanolic extract of Schinus molle obtained in accordance with Example 2

| mQPA-NHEK-BARRIER-16 | Genes Full name and abbreviation | | Control Cycles | 0.0001% | | 0.0003% | | 0.001% | |
|---|---|---|---|---|---|---|---|---|---|
| | | | | Cycles | % Control (mean HK)) 100 | Cycles | % Control (mean HK) 100 | Cycles | % control (mean HK) 100 |
| | 3-phosphate dehydrogenase | | 16.91 | 17.12 | | 17.10 | | 17.11 | |
| Hydration, transport of solutes | Aquaporin 3 (Gill blood group) | AQP3 | 22.95 23.06 | 23.75 23.73 | 73 | 23.24 23.08 | 111 | 22.66 22.58 | 172 |
| Extra-cellular matrix | Hyaluronan synthase 3 | HAS3 | 25.15 25.28 | 25.82 25.87 | 78 | 26.43 26.15 | 59 | 26.50 26.52 | 54 |
| Lipid synthesis | Acyl-CoA synthetase short-chain family member 2 | ACSS2 | 23.42 23.57 | 23.78 23.78 | 100 | 23.83 23.73 | 101 | 23.85 23.76 | 106 |
| | Fatty acid synthase | FASN | 21.30 21.32 | 22.00 21.93 | 77 | 21.98 21.88 | 80 | 22.25 22.22 | 69 |
| | Serine palmitoyltransferase, long chain base subunit 1 | SPTLC1 | 24.19 24.15 | 24.65 24.71 | 85 | 24.10 24.11 | 129 | 24.29 24.45 | 115 |
| | LAG1 homolog, ceramide synthase 6 | LASS6 | 27.52 27.65 | 27.68 27.77 | 110 | 27.70 27.87 | 108 | 27.25 27.41 | 157 |
| | UDP-glucose ceramide glucosyltransferase | UGCG | 25.91 25.93 | 25.71 25.52 | 150 | 26.19 25.93 | 112 | 25.96 25.86 | 133 |
| | Sphingomyelin phosphodiesterase 1, acid lysosomal | SMPD1 | 26.81 26.89 | 28.34 28.60 | 40 | 28.57 28.66 | 36 | 28.15 28.19 | 53 |
| | Glucosidase, beta; acid (includes glucosylceramidase) | GBA | 24.97 25.09 | 25.18 25.15 | 110 | 25.33 25.41 | 97 | 25.43 25.62 | 94 |
| | Sulfotransferase family, cytosolic, 2B, member 1 | SULT2B1 | 25.42 25.52 | 26.59 26.43 | 59 | 25.72 25.77 | 102 | 25.08 25.30 | 160 |
| | Arachidonate 12-lipoxygenase | ALOX12 | 27.73 27.57 | 28.93 28.92 | 50 | 29.31 28.94 | 45 | 28.59 28.79 | 64 |
| Keratinocyte differentiation | Claudin 1 | CLDN1 | 22.78 22.84 | 23.50 23.50 | 75 | 22.71 22.96 | 122 | 22.21 22.28 | 195 |
| | Filaggrin | FLG | 25.12 24.98 | 25.51 25.29 | 95 | 25.21 25.14 | 113 | 24.94 24.64 | 158 |
| | Involucrin | IVL | 24.86 24.95 | 25.70 25.82 | 67 | 25.13 25.47 | 94 | 25.54 25.47 | 87 |
| | Transglutaminase 1 (K polypeptide epidermal type I, protein-glutamine-gamma-glutamyltransferase) | TGM1 | 28.06 28.28 | 29.03 28.74 | 74 | 28.29 28.15 | 119 | 27.81 27.60 | 182 |

TABLE 2

CaCl$_2$ - 1.5 mM

| mQPA-NHEK-BARRIER-16 | Genes Full name and abbreviation | | Control Cycles | Cycles | % Control (RPS28) | % Control (GAPDH) | % Control (mean HK) 100 |
|---|---|---|---|---|---|---|---|
| Housekeeping genes (HK) | Ribosomal protein S28 | RPS28 | 18.79 18.81 | 19.13 19.13 | 100 | 96 | 97 |
| | Glyceraldehyde-3-phosphate dehydrogenase | GAPDH | 16.77 16.91 | 17.16 17.06 | 104 | 100 | 101 |
| Hydration, transport of solutes | Aquaporin 3 (Gill blood group) | AQP3 | 22.95 23.06 | 23.18 23.09 | 115 | 110 | 111 |
| Extracellular matrix | Hyaluronan synthase 3 | HAS3 | 25.15 25.28 | 25.34 25.42 | 112 | 108 | 108 |

TABLE 2-continued

| | | | CaCl$_2$ - 1.5 mM | | | | |
|---|---|---|---|---|---|---|---|
| mQPA-NHEK-BARRIER-16 | Genes Full name and abbreviation | | Control Cycles | Cycles | % Control (RPS28) | % Control (GAPDH) | % Control (mean HK) 100 |
| Lipid synthesis | Acyl-CoA synthetase short-chain family member 2 | ACSS2 | 23.42 23.57 | 23.34 23.51 | 132 | 127 | 128 |
| | Fatty acid synthase | FASN | 21.30 21.32 | 21.51 21.51 | 109 | 105 | 106 |
| | Serine palmitoyltransferase, long chain base subunit 1 | SPTLC1 | 24.19 24.15 | 24.58 24.46 | 99 | 95 | 96 |
| | LAG1 homolog, ceramide synthase 6 | LASS6 | 27.52 27.65 | 27.80 27.83 | 107 | 103 | 104 |
| | UDP-glucose ceramide glucosyltransferase | UGCG | 25.91 25.93 | 25.96 25.94 | 123 | 118 | 119 |
| | Sphingomyelin phosphodiesterase 1, acid lysosomal | SMPD1 | 26.81 26.89 | 27.01 27.00 | 113 | 108 | 109 |
| | Glucosidase, beta; acid (includes glucosylceramidase) | GBA | 24.97 25.09 | 24.96 25.04 | 128 | 123 | 124 |
| | Sulfotransferase family, cytosolic, 2B, member 1 | SULT2B1 | 25.42 25.52 | 24.44 24.47 | 254 | 244 | 246 |
| | Arachidonate 12-lipoxygenase | ALOX12 | 27.73 27.57 | 27.18 27.48 | 158 | 151 | 152 |
| Keratinocyte differentiation | Claudin 1 | CLDN1 | 22.78 22.84 | 22.55 22.53 | 152 | 145 | 147 |
| | Filaggrin | FLG | 25.12 24.98 | 24.79 24.66 | 157 | 151 | 152 |
| | Involucrin | IVL | 24.86 24.95 | 24.42 24.31 | 183 | 175 | 177 |
| | Transglutaminase 1 (K polypeptide epidermal type I, protein-glutamine-gamma-glutamyltransferase) | TGM1 | 28.06 28.28 | 27.01 26.96 | 285 | 274 | 276 |

In Tables 1 and 2, it is considered that there is stimulation when the % is greater than or equal to 150. By contrast, it is considered that there is inhibition when the % is lower than or equal to 65%.

The incubation of the NHEKs with the positive reference of differentiation CaCl$_2$ at 1.5 mM increased the expression of the mRNAs coding for the markers of lipid synthesis (SULT2B1 and ALOX12) and of keratinocyte differentiation (FLG, IVL and TGM1). These results were expected and made it possible to validate the test.

The hydroethanolic extract of Schinus molle obtained in accordance with Example 2, at the stronger concentration tested (0.001%), stimulated the expression of the markers of keratinocyte differentiation CLDN1, FLG and TGM1. In addition, an increase in the expression of the marker of hydration AQP3 and of the markers of lipid synthesis LASS6 and SULT2B1 was also observed. This was associated with a decrease in the expression of certain genes involved in lipid synthesis (SMPD1 and ALOX12). At the two lowest concentrations tested (0.0001% and 0.0003%), only inhibition of the expression of SMPD1 and ALOX12 was observed.

Conclusion

In the experimental conditions of this study, the results obtained suggest that the hydroethanolic extract of Schinus molle obtained in accordance with Example 2, at the stronger concentration tested (0.001%), appears to have a positive effect on the hydration and barrier function of the epidermis.

EXAMPLE 5: EVALUATION OF THE PROTECTIVE EFFECT OF THE EXTRACT OF SCHINUS MOLLE IN ACCORDANCE WITH EXAMPLE 1 ON KERATINOCYTES EXPOSED TO ENVIRONMENTAL STRESS BY PM10-LIKE POLLUTING PARTICLES

The objective of this study is to determine the protective effect of the extract of Schinus molle according to Example 1 at 0.1% on keratinocytes exposed to an environmental stress. The pollution of the air is associated with the presence of fine particles having a size smaller than 10 μM (PM10-like particles).

The cell stress is measured by measuring the enzyme activity of lactate dehydrogenase (LDH) released into the extracellular medium by the cells. LDH is an oxyreductase enzyme which catalyses the conversion of pyruvate into lactate. The cells release this enzyme into the extracellular medium when cell integrity has been compromised.

This enzymatic test has been widely used to evaluate the presence of lesions and toxicity of tissues and cells.

Protocol:

Normal human keratinocytes are cultivated in medium without serum, then treated with an extract of *Schinus molle* in accordance with Example 1 at 0.1% diluted in the culture medium for 48 h at a rate of 2 applications per day. The untreated control is produced under the same conditions. At the end of 48 h, PM10-like polluting particles are applied to the cells at two concentrations, 250 µg/ml or 500 µg/ml, over 24 h with a single application.

The next day, the extracellular medium is sampled so as to measure the enzyme activity of the lactate dehydrogenase using the strict and detailed protocol of the Lactate Dehydrogenase Activity Assay Kit (Sigma-aldrich, MAK066). Each condition is produced in triplicate.

Results:

The results presented in FIG. 1 obtained in vitro show that the extract of *Schinus molle* according to Example 1 at 0.1% protects, in a highly significant manner, the keratinocytes exposed to stress by PM10-like particles at doses of 250 µg/ml (−29.6% of LDH released compared to the PM10-like treatment 250 µg/ml) and 500 µg/ml (−38.5% of LDH released compared to the PM10-like treatment 500 µg/ml).

EXAMPLE 6: EVALUATION OF THE PROTECTIVE EFFECT OF THE EXTRACT OF *SCHINUS MOLLE* IN ACCORDANCE WITH EXAMPLE 1 ON KERATINOCYTES EXPOSED TO ENVIRONMENTAL STRESS BY PM2.5-LIKE POLLUTING PARTICLES

The objective of this study is to determine the protective effect of the extract of *Schinus molle* according to Example 1 at 0.1% on keratinocytes exposed to environmental stress. The cell stress is measured by measuring the enzyme activity of lactate dehydrogenase (LDH) released into the extracellular medium by the cells. LDH is an oxyreductase enzyme which catalyses the conversion of pyruvate into lactate. The cells release this enzyme into the extracellular medium when cell integrity has been compromised. The pollution of the air is associated with the presence of fine particles having a size smaller than 10 µM (PM10-like particles), but also with the presence of particles of small size, smaller than or equal to 2.5 µM (PM2.5-like). Their size being smaller than that of the pores of the skin, PM2.5-like particles can induce damage directly.

Protocol:

Normal human keratinocytes are cultivated in medium without serum, then treated with an extract of *Schinus molle* in accordance with Example 1 at 0.1% diluted in the culture medium for 48 h at a rate of 2 applications per day. The untreated control is produced under the same conditions. At the end of 48 h, PM2.5-like polluting particles are applied to the cells in a concentration of 100 µg/ml over 24 h with a single application.

The next day, the extracellular medium is sampled so as to measure the enzyme activity of the lactate dehydrogenase using the strict and detailed protocol of the Lactate Dehydrogenase Activity Assay Kit (Sigma-aldrich, MAK066). Each condition is produced in triplicate.

Figure 2:
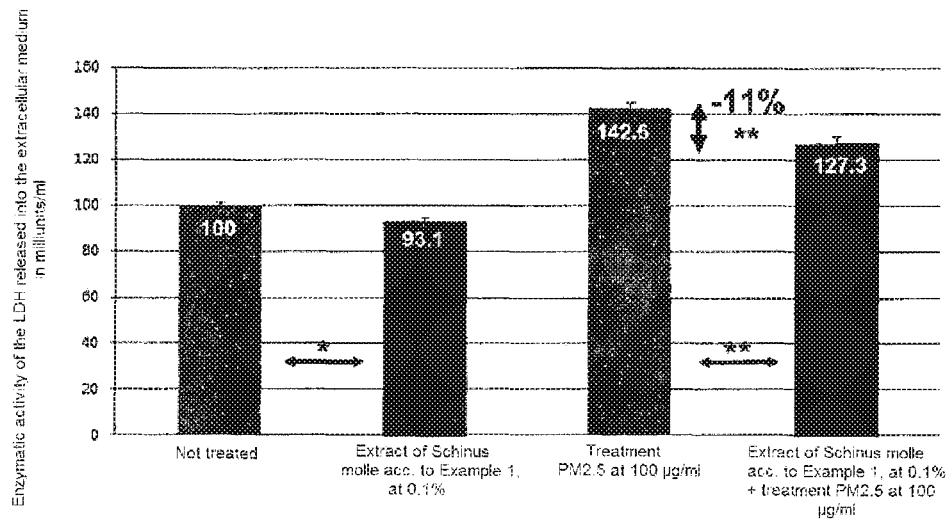
FIG. 2 shows the evaluation of the protective effect of an extract of *Schinus molle* according to the invention on keratinocytes exposed to an environmental stress by PM2.5-like polluting particles.

Results:

The results presented in FIG. 2 obtained in vitro show that the extract of *Schinus molle* according to Example 1 at 0.1% protects, in a highly significant manner, the keratinocytes exposed to stress by PM2.5-like particles at a dose of 100 µg/ml (−11% of LDH released compared to the PM2.5-like treatment 100 µg/ml).

EXAMPLE 7: EVALUATION OF THE EFFECT OF THE EXTRACT OF *SCHINUS MOLLE* ACCORDING TO EXAMPLE 1 ON THE LEVEL OF EXPRESSION OF EPIGENETIC MARKERS AND OF mRNA INVOLVED IN THE BARRIER FUNCTION OF THE SKIN

The objective of this study is to determine the effect of the extract of *Schinus molle* according to Example 1 at 0.1% on the levels of expression of two long non-coding RNAs (epigenetic modulators of the barrier function of the skin): TINCR (Tissue differentiation-Inducing Non-protein Coding RNA) and DANCR (Differentiation Antagonizing Non-protein Coding RNA), as well as the levels of expression of mRNA coding for proteins involved in the barrier function of the skin, such as: E-cadherin (CDH1), involucrin (IVL), transglutaminase-1 (TGM1) and caspase 14 (CASP14) in normal human keratinocytes.

Protocol:

Normal human keratinocytes are cultivated in a medium without serum, then treated with an extract of *Schinus molle* according to Example 1 at 0.1% diluted in the culture medium over 48 h at a rate of 2 applications per day. The untreated control is produced under the same conditions.

The total mRNAs are extracted with the aid of a miRVana extraction kit (Ambion, AM1561), then reverse transcription is performed with the aid of the High Capacity cDNA reverse transcription kit (Applied Biosystem, 4374966) for each of the conditions. Quantitative PCR in real time is performed using the TaqMan® Gene Expression Assays specific for DANCR (Applied Biosystem: 4426961; Hs03653830_g1), TINCR, TGM1, IVL and CASP14 (Applied Biosystem: 4331182; Hs00542141_m1, Hs01070310_m1, Hs00846307_s1, Hs00201637_m1) and the TaqMan® Gene Expression Master Mix reaction buffer (Applied Biosystem: 4369514), in a StepOne Plus thermocycler (Applied Biosystem). The TaqMan® Gene Expression Assay specific for 18S is used as endogenic control (Applied Biosystem: 4331182; Hs99999901_s1). The relative quantification of the expression of the different mRNAs is performed by the comparative Ct method. The results are given in percentage of increase in the level of expression in relation to the controlled condition.

Results (Table) and Conclusions:

| Barrier function of the skin | | | | | |
|---|---|---|---|---|---|
| Epigenetic biological markers | | Biological markers: mRNA | | | |
| DANCR | TINCR | E-Cadherin | Involucrin | Transglutaminase-1 | Caspase 14 |
| −26% | +65% | +34% | +283% | +185% | +152% |

The results displayed in the table above show that the extract of *Schinus molle* according to Example 1 at 0.1% positively modulates the epidermal expression, in vitro. The extract of *Schinus molle* according to Example 1 at 0.1% increases, in vitro, the expression of the mRNAs coding for E-cadherin, involucrin, transglutaminase-1 and caspase 14, these proteins being involved in the barrier function of the skin.

EXAMPLE 8: EVALUATION OF THE EFFECT OF THE EXTRACT OF SCHINUS MOLLE ACCORDING TO EXAMPLE 1 ON THE CELL COHESION OF THE SKIN BARRIER BY THE STUDY OF CLAUDINE 1

The objective of this study is to evaluate the effect of the extract of Schinus molle according to Example 1 at 1% on the expression of the protein claudine 1 involved in the epidermal tight junctions. Claudine 1 forms an expression gradient in the epidermis. The tight junctions are dynamic structures which assure the cell cohesion and the barrier function of the skin.

Protocol:

Biopsies of human skin measuring 6 mm in diameter are kept in culture ex vivo in the presence of a specific medium (DMEM 1 g/L, HAMF12, SVF and antibiotics) on inserts deposited in 6-well plates. The biopsies are cultivated for 48 h and receive 2 applications per day of the extract of Schinus molle according to Example 1 diluted at 1% in PBS 1×, or just PBS 1× for the controlled condition. The biopsies are then fixed in formaldehyde, then enclosed in paraffin. Skin sections of 4 µm thickness are then taken. Immunomarking is then performed with the aid of a rabbit polyclonal antibody specific to claudine 1 (Abcam, ab15098), then a secondary anti-rabbit antibody coupled to a fluorochrome (Invitrogen, A21206). The biopsies are then examined under epifluorescence microscope (Zeiss Axiovert 200M microscope). Quantification of the fluorescence, with the aid of Volocity® image analysis software (PerkinElmer, Inc.), was performed on the basis of the photographs obtained.

Results and Conclusions:

The treatment with the extract of Schinus molle according to Example 1 at 1% makes it possible to observe a highly significant rise in the expression of claudine 1 of 128.2% compared to the controlled condition treated just with PBS 1×, for the ex vivo study (Student's t-test, n=3+/−sme (sme: standard mean error)).

The treatment by the extract of Schinus molle according to Example 1 at 1% caused an improved cohesion of the most differentiated layers of the epidermis and thus reinforced the skin barrier function.

EXAMPLE 9: EVALUATION OF THE EFFECT OF THE EXTRACT OF SCHINUS MOLLE ACCORDING TO EXAMPLE 1 ON THE CELL COHESION UNDERLYING THE SKIN BARRIER FUNCTION BY STUDYING HYALURONIC ACID ON BIOPSIES EX VIVO

The objective of this study is to evaluate the effect of the extract of Schinus molle according to Example 1 at 1% on the expression of the hyaluronic acid involved in the establishment of the skin barrier. Hyaluorinic acid is abundant in the extracellular matrices and also contributes to the hydrodynamism of the epidermis by modulating the epidermal differentiation, and to the improvement of the repair of the skin.

Protocol:

Human skin biopsies measuring 6 mm in diameter are kept in culture ex vivo in the presence of a specific medium (DMEM 1 g/L, HAMF12, SVF and antibiotics) on inserts deposited in 6-well plates. The biopsies are cultivated for 48 h and receive 2 applications per day of the extract of Schinus molle according to Example 1 diluted at 1% in PBS 1×, or just PBS 1× for the controlled condition. The biopsies are then fixed in formaldehyde, then enclosed in paraffin. Skin sections of 4 µm thickness are then taken. The hyaluronic acid is then detected with the aid of a biotinylated hyaluronic acid binding protein (Coger—Seikagaki America, 400-763-1A), then with the aid of a streptavidin coupled to a fluorochrome (Invitrogen, S32354). The biopsies are then examined under epifluorescence microscope (Zeiss Axiovert 200M microscope). Quantification of the fluorescence, with the aid of Volocity® image analysis software (PerkinElmer, Inc.), was performed on the basis of the photographs obtained.

Results and Conclusions:

The treatment with the extract of Schinus molle according to Example 1 at 1% makes it possible to observe a highly significant rise in hyaluronic acid in the dermis and epidermis of 58.9% compared to the controlled condition treated just with PBS 1×, for the ex vivo study (Student's t-test, n=3+/−sme.

The treatment by the extract of Schinus molle according to Example 1 at 1% caused an improvement of the skin barrier function.

EXAMPLE 10: EVALUATION OF THE PROTECTIVE EFFECT OF THE EXTRACT OF SCHINUS MOLLE ACCORDING TO EXAMPLE 1 ON THE LIPID CONTENT OF KERATINOCYTES IN CULTURE

The objective of this study is to determine the effect of the extract of Schinus molle according to Example 1 at 0.1% on the lipid content of keratinocytes, which underlies the skin barrier function.

Protocol:

Normal human keratinocytes are cultivated in medium without serum, then treated with an extract of Schinus molle according to Example 1 at 0.1% diluted in the culture medium for 48 h at a rate of 2 applications per day. The untreated control is produced under the same conditions. At the end of 48 h, the cells are fixed with formaldehyde at 3.7% for 10 minutes (Sigma-aldrich, F1635). After rinsing with PBS, the cells are contacted with Nile Red at 100 nM for 10 minutes (Sigma-aldrich, N3013) before being rinsed with PBS 1×. The cells are then examined under epifluorescence microscope (Zeiss Axiovert 200M microscope).

Fluorescence quantification, with the aid of Volocity® image analysis software (PerkinElmer, Inc.), was performed on the basis of the photographs obtained.

Results:

The microscopic observations show a highly significant fluorescence with the extract of Schinus molle according to Example 1 at 0.1% for the lipid synthesis of keratinocytes (+102% compared to the untreated sample (according to the Student's t-test, n=3+/−sme)).

The treatment with extract of Schinus molle according to Example 1 at 0.1% seems to allow a reinforcement of the skin barrier function.

EXAMPLE 11: EVALUATION OF THE EFFECT OF THE EXTRACT OF SCHINUS MOLLE ACCORDING TO EXAMPLE 1 ON THE CELL COHESION OF THE SKIN BARRIER BY STUDYING LIPIDS OF THE EPIDERMIS ON BIOPSIES EX VIVO

The objective of this study is to evaluate the effect of the extract of Schinus molle according to Example 1 at 1% on the lipid content of the epidermis. The lipids forming the epidermis have an important role in maintaining the barrier function and in the protection thereof against external attacks.

Protocol:

Biopsies of human skin measuring 6 mm in diameter are kept in culture ex vivo in the presence of a specific medium (DMEM 1 g/L, HAMF12, SVF and antibiotics) on inserts deposited in 6-well plates. The biopsies are cultivated for 48 h and receive 2 applications per day of the extract of Schinus molle according to Example 1 diluted at 1% in PBS 1×, or just PBS 1× for the controlled condition. The biopsies are then fixed in formaldehyde, then enclosed in paraffin. Skin sections of 4 µm thickness are then taken. The lipid content of the epidermis is then detected with the aid of a solution of Nile Red at 100 nM (Sigma-aldrich, N3013) followed by incubation in an alkaline buffer. The biopsies are then examined under epifluorescence microscope (Zeiss Axiovert 200M microscope).

A quantification of the fluorescence, with the aid of Volocity® image analysis software (PerkinElmer, Inc.), was performed on the basis of the photographs obtained.

Results and Conclusions:

The treatment with the extract of *Schinus molle* according to Example 1 makes it possible to observe a very significant increase of the lipids in the epidermis of 41%, compared to the controlled condition treated just with PBS 1×, for the ex vivo study (Student's t test, n=3+/−sme).

The treatment with extract of *Schinus molle* according to Example 1 at 1% seems to allow a reinforcement of the skin barrier function.

EXAMPLE 12: EVALUATION OF THE EFFECT OF THE EXTRACT OF SCHINUS MOLLE ACCORDING TO EXAMPLE 1 ON THE BARRIER FUNCTION OF THE SKIN AFTER SDS STRESS

The objective of this study is to evaluate, in vitro, on reconstructed tissues, the effect of the extract of *Schinus molle* according to Example 1 at 1% on the permeability of the skin after SDS stress using a fluorescent dye.

Protocol:

Reconstructed human epidermises (RHE) are treated, from day 10 post-reconstruction, by topical application with an extract of *Schinus molle* according to Example 1 diluted at 1% in PBS 1× for 48 h at a rate of 2 applications per day. The control is treated with PBS 1× under the same conditions.

The RHE are then treated, on the $12^{th}$ day post-reconstruction, with SDS at 0.15% for 3 h then rinsed 5 times with PBS 1×. The RHE are then treated with 1 mM of lucifer yellow (Fluka, 62644), a fluorescent dye, for 2 h. The RHE are rinsed with PBS 1× and then fixed in formaldehyde and enclosed in paraffin. Skin sections of 4 µm thickness are then taken and deposited on slides. The slides are then removed of paraffin and passed through a number of successive alcohol baths.

The penetration of the dye through the barrier and into the tissue is observed under epifluorescence microscope (Zeiss Axiovert 200M microscope). The diffusion of the fluorescence through the epidermis is evaluated on the basis of the photographs obtained with the aid of Volocity® image analysis software (PerkinElmer, Inc.).

Results and Conclusions:

The RHE pre-treated with an extract of *Schinus molle* according to Example 1 at 1% and stressed with 0.15% SDS allow the dye to penetrate to a lesser extent. A significant reduction of 16% of the diffusion of the dye into the epidermis compared to the conditions treated with PBS 1× and stressed with 0.15% SDS was observed (Student's t-test, "SDS 0.15%" n=4, "1%+SDS" n=7, mean±sme).

The treatment with the extract of *Schinus molle* according to Example 1 at 1% seems to allow a reinforcement of the skin barrier function.

EXAMPLE 13: EFFECT OF THE EXTRACT OF SCHINUS MOLLE FORMULATED ACCORDING TO EXAMPLE 3 ON THE REGULATION OF SEBUM SECRETION—STUDY IN VIVO

Objective: study in vivo of the effect of an extract of *Schinus molle* formulated according to Example 3 on the regulation of sebum secretion in healthy volunteers against the placebo composition.

Number of healthy volunteers: 10 (aged from 24 to 46 years).

Study: double-blind study against placebo.

Products tested: Extract of *Schinus molle*, formulated at 1% in a composition (formula reference #TCAAE08) according to Example 3 versus the placebo composition.

Number of applications: 2 applications per day, morning and evening, at a dose of 2 mg/cm².

Test duration: 3 weeks.

Monitoring visits: d0, d0-t1 h, d7 and d21.

Measurements:

The physiological secretion of sebum, that is to say in non-pathological conditions, is evaluated by the application of Sebutape®, an opaque white adhesive permeable to sebum, to the skin of the volunteers. The zones that are in contact with the sebum form transparent "spots". The quantitative analysis of the surface and the number of spots present on the Sebutapes is performed with the aid of the software Quantiseb®. The size of the pores is evaluated independently on the basis of photos with the aid of a DermaTop®.

Statistical analyses: Student's "t"-test.

Figure 3:
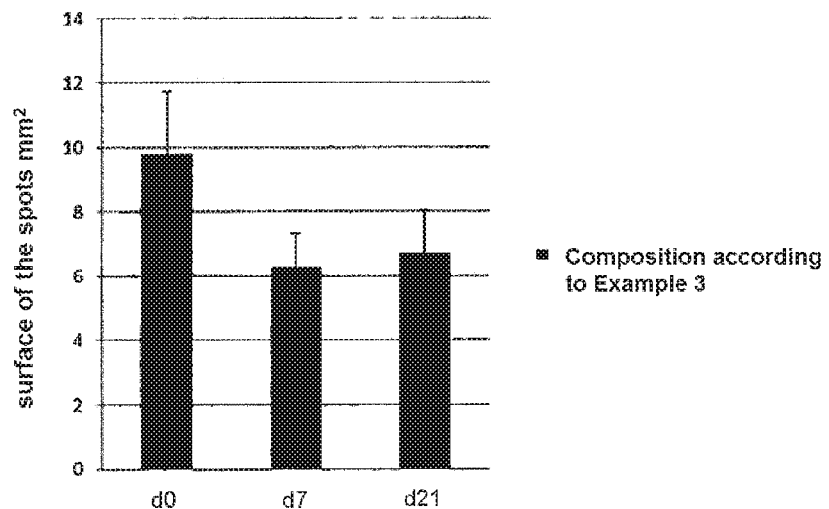
FIG. 3 shows the effect of an extract of *Schinus molle* according to the invention on the regulation of sebum secretion by measurement of the surface of the spots.
Figure 4:
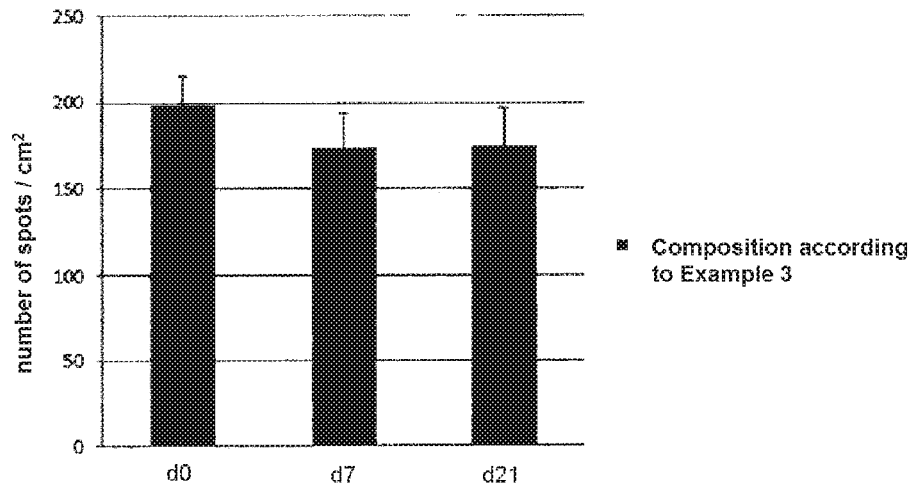
FIG. 4 shows the development of sebum secretion by measurement of the number of spots after application of an extract of *Schinus molle* according to the invention.

Results:

After application of the composition (reference #TCAAE08) comprising an extract of *Schinus molle* formulated at 1% according to Example 3, the analysis shows a statistically significant reduction on d7 and d21 of the surface of the spots (FIG. 3 and Table 3) and of the number of spots/cm² (FIG. 4 and Table 4).

TABLE 3

Development of sebum secretion (measurement of the surface of the spots) after application of the composition containing the extract of *Schinus molle* at 1% according to Example 3

| Treatment | Time | Mean (mm²) | sme | p | % change | % of volunteers having experienced a reduction of sebum secretion |
|---|---|---|---|---|---|---|
| Placebo | d7-d0 | 3.26 | 0.97 | 0.0004*** | −81% | 100 |
| Formula reference #TCAAE08 (Extract of *Schinus molle* at 1% according to Example 3) | d7-d0 | −3.59 | 1.1 | | | |

TABLE 3-continued

Development of sebum secretion (measurement of the surface of the spots) after application of the composition containing the extract of Schinus molle at 1% according to Example 3

| Treatment | Time | Mean (mm$^2$) | sme | p | % change | % of volunteers having experienced a reduction of sebum secretion |
|---|---|---|---|---|---|---|
| Placebo | d21-d0 | 3.04 | 1.19 | 0.0051** | −72.6% | 90 |
| Formula reference #TCAAE08 (Extract of Schinus molle at 1% according to Example 3) | d21-d0 | −3.09 | 1.46 | | | |

**very significant;
***highly significant with the Student's test;
mean n = 10 +/− sme (standard mean error).

TABLE 4

Development of sebum secretion (measurement of the number of spots) after application of the composition containing the extract of Schinus molle at 1% according to Example 3

| Treatment | Time | Mean (number/cm$^2$) | sme | p | % change | % of volunteers having experienced a reduction in the number of spots |
|---|---|---|---|---|---|---|
| Placebo | d7-d0 | 50.32 | 15.09 | 0.0061** | −40% | 90 |
| Formula reference #TCAAE08 (Extract of Schinus molle at 1% according to Example 3) | d7-d0 | −24.06 | 14.58 | | | |
| Placebo | d21-d0 | 45.68 | 11.23 | 0.0033*** | −37.2% | 80 |
| Formula reference #TCAAE08 (Extract of Schinus molle at 1% according to Example 3) | d21-d0 | −22.96 | 16.86 | | | |

**very significant;
***highly significant with the Student's test;
mean n = 10 +/− sme (standard mean error).

In addition, the photos of the DermaTop (not shown) show a visible effect on the reduction of the size of the pores and number thereof 1 hour after application (d0-t1 h) of the composition (formula reference #TCAAE08) comprising an extract of Schinus molle according to Example 3 compared to the placebo.

EXAMPLE 14: EFFECT OF AN EXTRACT OF SCHINUS MOLLE FORMULATED ACCORDING TO EXAMPLE 3 ON THE APPEARANCE OF WRINKLES—STUDY IN VIVO

Objective: study of the effect of an extract of Schinus molle formulated according to Example 3 on the appearance of wrinkles compared to the placebo composition.

Number of volunteers: 14, 4 of which left the study. The test was analysed on 10 volunteers aged from 52 to 64 years.

Study: double-blind study against placebo.

Products tested: Extract of Schinus molle, formulated at 1% in a composition (formula reference #TCAAE08) according to Example 3 versus the placebo composition.

Number of applications: 2 applications per day, morning and evening, at a dose of 2 mg/cm$^2$.

Duration of the test: 8 weeks.

Monitoring visits: d0 and d56.

Measurements:

The number and depth of the wrinkles are analysed on silicone replicas taken at crow's feet with the aid of the software Quantirides®. The visual appearance is evaluated by colour photos of the crow's feet with the aid of the photo bench HeadScan®.

Statistical analyses: depending on the normality of distribution of the data, the Student's "t"-test or the Wilcoxon test was used.

Figure 5:
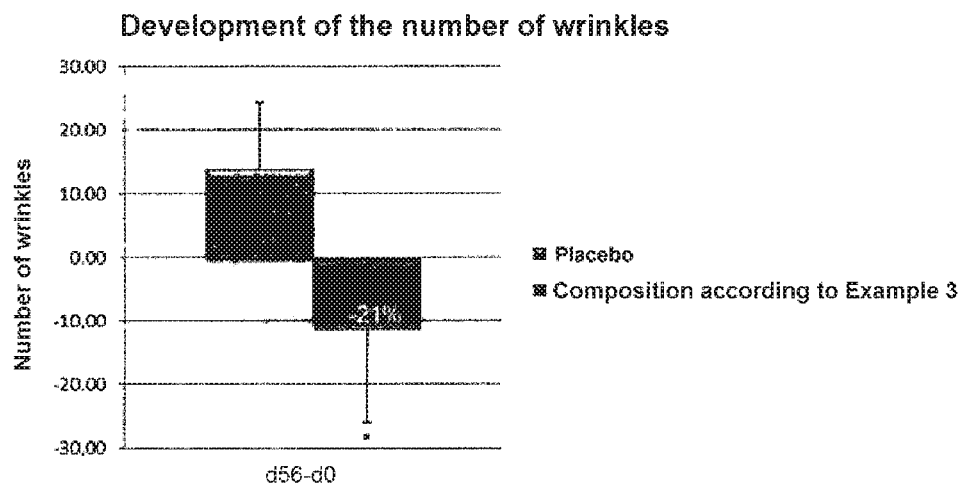
FIG. 5 shows the effect of an extract of *Schinus molle* according to the invention on the development of the number of wrinkles.
Figure 6:
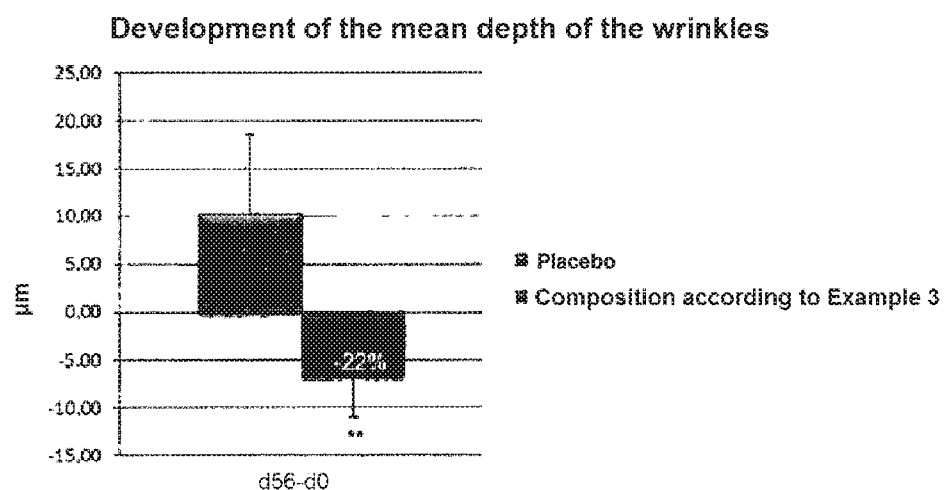
FIG. 6 shows the effect of an extract of *Schinus molle* according to the invention on the development of the average depth of wrinkles.

Results:

After application of the composition (reference #TCAAE08) comprising an extract of Schinus molle formulated at 1% according to Example 3, a statistically significant reduction on d56 of the number of wrinkles (FIG. 5 and Table 5) and of the mean depth of the wrinkles (FIG. 6 and Table 5) are observed compared to the placebo.

TABLE 5

Study of the effect of an extract of *Schinus molle* formulated according to Example 3 on the number of wrinkles and their mean depth

| | Treatment | Time | Mean | sme | p | % change | % of volunteers improved |
|---|---|---|---|---|---|---|---|
| Number of wrinkles | Placebo | day 56-day 0 | 13.9 | 10.39 | 0.0304* | −21.16 | |
| | Formula reference #TCAAE08 comprising an extract of *Schinus molle* according to Example 3, formulated at 1% | day 56-day 0 | −10.8 | 15.35 | | | 70% (7/10) |
| Mean depth (μm) | Placebo | day 56-day 0 | 10.28 | 8.33 | 0.0068** | −22.29 | |
| | Formula reference #TCAAE08 comprising an extract of *Schinus molle* according to Example 3, formulated at 1% | day 56-day 0 | −6.59 | 4.4 | | | 80% (8/10) |

*significant;
**very significant;
with the Student test or the Wilcoxon test (test selected depending on the normality of distribution of the data);
mean n = 10 +/− sme (standard mean error).

In addition, the colour photos (not shown) show an apparent reduction in the wrinkles on d56 after application of the composition (reference #TCAAE08) comprising an extract of *Schinus molle* according to Example 3, formulated at 1% compared to the placebo.

EXAMPLE 15: TEST PROTOCOL OF AN EXTRACT OF *SCHINUS MOLLE* ACCORDING TO EXAMPLE 3, FORMULATED AT 1%: HYDRATING EFFECT—STUDY IN VIVO

Objective: study of the hydrating effect of an extract of *Schinus molle* according to Example 3, formulated at 1% compared to the placebo composition.

Number of volunteers: 10 (aged from 24 to 40 years).
Study: double-blind study against placebo.
Products tested: Extract of *Schinus molle*, formulated at 1% in a composition (Formula reference #TCAAE08) according to Example 3 versus the placebo composition.

Number of applications: 1 application at a dose of 2 mg/cm$^2$.

Test duration: 3 h.

Monitoring visits: T0, T30 min, T1 h, T1 h30, T2 h, T2 h30, T3 h.

Measurements: quantitative measurement of the hydration with the aid of a Corneometer® CM825 and visual evaluation by an expert and by the volunteers.

Statistical analysis: depending on the normality of the data, the Student's "t"-test or Wilcoxon test was used.

Figure 7:
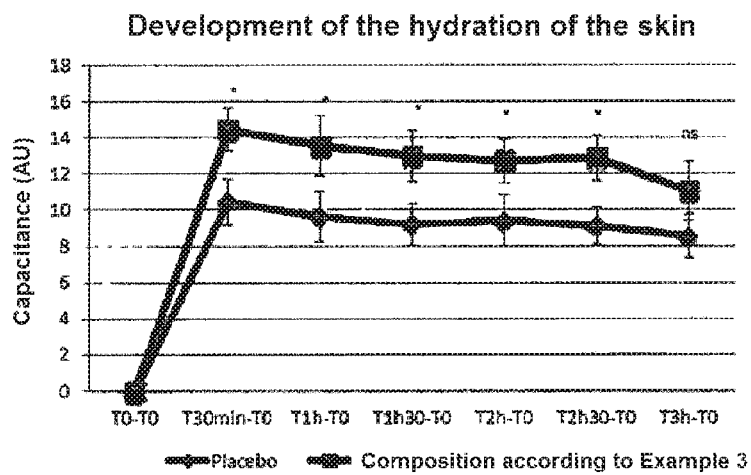
FIG. 7 shows the effect of an extract of *Schinus molle* according to the invention on the development of the hydration of the skin.

Results:

A significant increase was observed in the hydration (FIG. 7 and Table 6) from 30 minutes after the application of the composition (reference #TCAAE08) comprising an extract of *Schinus molle* according to Example 3, formulated at 1%, compared to the placebo.

TABLE 6

Study of the development of hydration of the skin after application of an extract of *Schinus molle* formulated according to Example 3

| Treatment | Time | Mean (AU) | sme | p | % of volunteers improved |
|---|---|---|---|---|---|
| Placebo | T30 min-T0 | 10.43 | 1.26 | 0.0107* | 80% (8/10) |
| Formula reference #TCAAE08 (example 3) | | 14.43 | 1.17 | | |
| Placebo | T1 h-T0 | 9.6 | 1.38 | 0.0190* | 70% (7/10) |
| Formula reference #TCAAE08 (example 3) | | 13.53 | 1.69 | | |
| Placebo | T1 h30-T0 | 9.2 | 1.16 | 0.0263* | 80% (8/10) |
| Formula reference #TCAAE08 (example 3) | | 12.97 | 1.44 | | |
| Placebo | T2 h-T0 | 9.4 | 1.44 | 0.0352* | 70% (7/10) |
| Formula reference #TCAAE08 (example 3) | | 12.7 | 1.23 | | |
| Placebo | T2 h30-T0 | 9.1 | 1.02 | 0.0103* | 80% (8/10) |
| Formula reference #TCAAE08 (example 3) | | 12.87 | 1.22 | | |

TABLE 6-continued

Study of the development of hydration of the skin after application
of an extract of Schinus molle formulated according to Example 3

| Treatment | Time | Mean (AU) | sme | p | % of volunteers improved |
|---|---|---|---|---|---|
| Placebo | T3 h-T0 | 8.53 | 1.22 | $0.0534^{ns}$ | 70% (7/10) |
| Formula reference #TCAAE08 (example 3) | | 11.03 | 1.64 | | |

$^{ns}$not significant;
*significant; with the Student test or the Wilcoxon test (test selected depending on the normality of distribution of the data);
mean n = 10 +/− sme (standard mean error).

Figure 8:
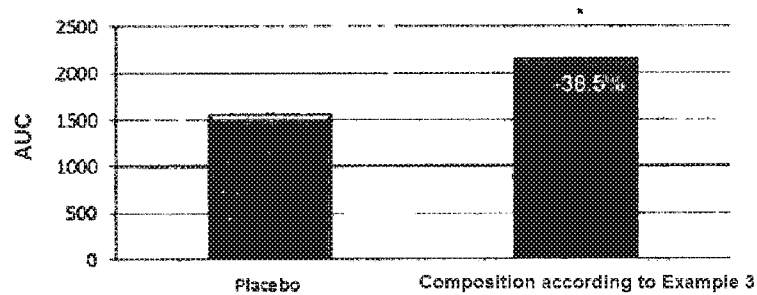
FIG. 8 shows the hydrating effect of an extract of *Schinus molle* according to the invention.

In addition, the calculation of the areas under the curve (AUC) show a significant hydrating effect over the duration of the study (FIG. 8 and Table 7).

TABLE 7

Study of the hydrating effect of an extract of
Schinus molle formulated according to Example 3

| Treatment | AUC | sme | P | % change | % of volunteers improved |
|---|---|---|---|---|---|
| Placebo | 1560 | 189.24 | 0.0129* | 38.49% | 70% (7/10) |
| Formula reference #TCAAE08 | 2160.5 | 211.43 | | | |

*significant with the Student test; AUC n = 10 +/− sme (standard mean error).

Of course, the invention is not limited to the embodiments and examples presented above, and a person skilled in the art, on the basis of routine activity, will be able to provide other embodiments not explicitly described, without departing from the scope of the invention.

The invention claimed is:

1. A cosmetic composition comprising, as protective active agent, an effective amount of an enriched hydroalcoholic extract of Schinus molle and a physiologically acceptable excipient,
    wherein, the enriched hydroalcoholic extract of Schinus molle comprises about 20% or less of extracted polyphenols by weight of the total weight of the enriched extract, with predominantly quercitrin and miquelianin among the extracted polyphenols in a concentration, respectively, of at least 0.04% of quercitrin by weight of the total weight of the enriched extract, and of at least 0.02% of miquelianin by weight of the total weight of the enriched extract, the other extracted polyphenols, considered independently of one another, being present in trace form in a concentration of less than 0.01% (100 ppm) by weight of the total weight of the enriched extract, wherein the enriched hydroalcoholic extract of Schinus molle is obtained from dried and ground un-stripped leaves of Schinus molle of the small stems carrying the leaves by solid-liquid extraction, with stirring, of from 5% to 10% by weight of solid matter relative to the total weight used, in a hydroalcoholic solvent, the alcohol being selected from ethanol or propanediol, in a proportion between 60% and 80% by weight of alcohol relative to the total weight of the solvent, at a temperature between 20° C. and 70° C. for a period between 1 hour and 2 hours, and enrichment of quercitrin and miquelianin by separation of the liquid and solid phases, and removal of the solid phase, to result in the enriched liquid extract of Schinus molle comprising predominantly quercitrin and miquelianin among the extracted polyphenols,
    wherein the enriched hydroalcoholic extract of Schinus molle is present in the composition in a concentration of from 0.001 to 1% by weight relative to the total weight of the composition,
    wherein the cosmetic composition is formulated so as to be applied topically to the skin and is in the form of an oil-in-water emulsion, a water-in-oil emulsion, or multiple emulsions, a cream, a lotion, a milk, a serum, an ointment, a gel, a mousse or an aerosol.

2. The composition of claim 1, wherein the composition improves the barrier function of the skin and protects the skin against atmospheric pollutants.

3. The composition of claim 1, wherein the enriched hydroalcoholic extract of Schinus molle is present in the composition in a concentration of from 0.01 to 1% by weight relative to the total weight of the composition.

4. The composition of claim 1, wherein the obtained enriched hydroalcoholic liquid extract of Schinus molle is purified by microfiltration, ultrafiltration and/or nanofiltration, so as to further enrich the extract by concentrating quercitrin and miquelianin compared to the proteins and polysaccharides also extracted.

5. The composition of claim 1, wherein when the said enriched hydroalcoholic extract of Schinus molle is obtained using ethanol as the selected alcohol, then the obtained liquid extract of Schinus molle is dried so as to obtain a solid extract of Schinus molle.

* * * * *